(12) United States Patent
Moriyama et al.

(10) Patent No.: US 8,187,609 B2
(45) Date of Patent: May 29, 2012

(54) MYCOVIRUS, ATTENUATED STRAIN OF PHYTOPATHOGENIC FUNGUS, PLANT DISEASE CONTROLLING AGENT, METHOD OF PRODUCING MYCOVIRUS, METHOD OF ATTENUATING PHYTOPATHOGENIC FUNGUS AND METHOD OF CONTROLLING PLANT DISEASE

(75) Inventors: Hiromitsu Moriyama, Tokyo (JP); Toshiyuki Fukuhara, Tokyo (JP); Tsutomu Arie, Tokyo (JP); Tohru Teraoka, Tokyo (JP)

(73) Assignee: National University Corporation Tokyo University of Agriculture and Technology, Tokyo (JP)

( * ) Notice: Subject to any disclaimer, the term of this patent is extended or adjusted under 35 U.S.C. 154(b) by 0 days.

(21) Appl. No.: 12/863,707

(22) PCT Filed: Jan. 5, 2009

(86) PCT No.: PCT/JP2009/000003
§ 371 (c)(1),
(2), (4) Date: Sep. 23, 2010

(87) PCT Pub. No.: WO2009/093409
PCT Pub. Date: Jul. 30, 2009

(65) Prior Publication Data
US 2011/0020289 A1    Jan. 27, 2011

(30) Foreign Application Priority Data

Jan. 21, 2008 (JP) ................................. 2008-011012
Feb. 18, 2008 (JP) ................................. 2008-035405
Apr. 13, 2008 (JP) ................................. 2008-104181

(51) Int. Cl.
*A61K 39/12* (2006.01)
*C12Q 1/68* (2006.01)

(52) U.S. Cl. .................................. 424/204.1; 435/6.15

(58) Field of Classification Search ........................ None
See application file for complete search history.

(56) References Cited

U.S. PATENT DOCUMENTS
5,665,581 A    9/1997    Chen et al.

OTHER PUBLICATIONS

GenBank Accession # ABX79996, Putative RNA-Dependent RNA Polymerase (*Aspergillus* mycovirus 1816), Dec. 11, 2007.*
Zhao et al., Disease Phenotype of Virus-Infected *Helminthosporium victoriae* Is Independent of Overexpression of the Cellular Alcohol Oxidase/RNA-Binding Protein Hv-p68, 2006, Phytopathology, vol. 96, pp. 326-332.*
Choi et al., Hypovirulence of Chestnut Blight Fungus Conferred by an Infectious Viral cDNA, Science, Aug. 7, 1992, vol. 257, pp. 800-803.
Moleleki et al., "Transfection of *Diaporthe perjuncta* with *Diaporthe* RNA Virus", Applied and Environmental Microbiology, Jul. 2003, vol. 69, No. 7, pp. 3952-3956.
Nuss et al., "Hypovirulence: Mycoviruses at the Fungal-Plant Interface", Nature Reviews/Microbiology, Aug. 2005, vol. 3, pp. 632-642.
Preisig et al., "A novel RNA mycovirus in a hypovirulent isolate of the plant pathogen *Diaporthe ambigua*", Journal of General Virology, 2000, vol. 81, pp. 3107-3114.
Suzaki et al., Transmissibility of viral double-stranded RNA between strains of the violet root rot fungus *Helicobasidium mompa* and the potential for viral dsRNA infection to this fingus using monokaryotic strains, Mycoscience, 2003, vol. 44, pp. 139-147.

* cited by examiner

*Primary Examiner* — Benjamin P Blumel
(74) *Attorney, Agent, or Firm* — Birch, Stewart, Kolasch & Birch, LLP

(57) ABSTRACT

The present invention provides a novel mycovirus that suppresses phytopathogenic fungi and a novel method for controlling plant diseases. A novel mycovirus that is present endogenously in a predetermined rice blast fungus, has four types of double-stranded RNAs of 2.8 to 3.6 kb, and suppresses a phytopathogenic fungus has been found. This virus suppresses phytopathogenic fungi such as rice blast fungus.

8 Claims, 3 Drawing Sheets

MYCOVIRUS, ATTENUATED STRAIN OF PHYTOPATHOGENIC FUNGUS, PLANT DISEASE CONTROLLING AGENT, METHOD OF PRODUCING MYCOVIRUS, METHOD OF ATTENUATING PHYTOPATHOGENIC FUNGUS AND METHOD OF CONTROLLING PLANT DISEASE

TECHNICAL FIELD

The present invention relates to a novel mycovirus that suppresses a phytopathogenic fungus, and to genes, nucleic acids, and proteins related to the mycovirus, an attenuated phytopathogenic fungal strain incorporating the mycovirus, a plant disease control agent containing the above, a mycovirus production method, a method for attenuating phytopathogenic fungus, a method for controlling plant disease, etc.

BACKGROUND ART

As plant diseases, there are those caused by climate, soil, or other environmental cause, those caused by a virus, bacteria, fungus (filamentous fungus), or other infective cause, those caused by a physiological disorder, and those caused by a compounded cause of the above. Even presently, there are numerous plant diseases that are impediments to production of foods, flowers, flowering trees, timbers, etc., and many of these diseases are high in economic impact.

Among plant diseases, fungi represent one of the most important pathogenic factors. It is said that approximately 80% of plant diseases are caused by fungi.

For example, blast is one of the most important plant diseases and occurs in various parts of the world. The pathogen is rice blast fungus (scientific name: "*Magnaporthe oryzae*"), which is a type of mold (filamentous fungus). For rice blast fungus, a suitable temperature for growth, spore formation, and infection is around 25° C. and the fungus favors humid environments. Outbreak of this fungus thus occurs due to low summer temperatures, heavy rainfall, inadequate sunlight, and other climatic causes to bring about crop failure and quality degradation of rice and apply a serious impact on economy.

There are numerous other plant diseases that are caused by fungi and are high in economic impact, such as sheath blight, rust, powdery mildew, anthracnose, sclerotinia rot, downy mildew, gray mold, etc. Development of novel agricultural chemicals, breed improvement, etc., are thus being carried out even today (in regard to control of blast, see, for example, Patent Documents 1 and 2).

Mycoviruses, which are relevant to the present invention, shall now be described.

A virus that infects fungi is called a mycovirus. Among these, mycoviruses having double-stranded RNA as a genome have been reported. Many of these mycoviruses infect host fungi latently and have hardly any impact on characteristics of the host.

Mycoviruses having a double-stranded RNA as the genome are presently classified into five families, including Partitiviridae, Totiviridae, and Chrysoviridae. Partitiviridae viruses have two straight-chain double-stranded RNAs of substantially the same size inside a virus particle and have a total gene size of 4 to 6 kbp. Totiviridae viruses have a single straight-chain double-stranded RNA of 4 to 7 kbp inside a virus particle. Besides the above, in chestnut blight fungus (scientific name: "*Cryphonectria parasitica*"), a virus that is present endogenously in the fungus and having a double-stranded RNA of 9 to 13 kbp has been discovered (hypovirus, etc.).

Chrysoviridae viruses have a spherical, virus-like particle and double-stranded RNAs of four components. These viruses, like Partitiviridae and Totiviridae viruses, are known to have a region encoding RdRP (RNA-directed RNA polymerase; RNA-dependent RNA polymerase, the same applies hereinafter). As examples of viruses belonging to Chrysoviridae, Hv145SV ("*Helminthosporium victoriae* 145S virus," the same applies hereinafter), PcV ("*Pencillium chrysogenum* virus," the same applies hereinafter), AbV1 ("*Agaricus bisporus* virus 1," the same applies hereinafter), etc., are known (see Non-Patent Document 1, etc.)

Recently, with respect to specific plant diseases, methods for attenuating the pathogen by a mycovirus, etc., and using the attenuated pathogen to control the disease are being examined and have come to be put to practical use in part. For example, a method of using a full-length cDNA of viral double-stranded RNA that suppresses toxicity of chestnut blight fungus to attenuate the fungus and apply the attenuated fungus to control of chestnut blight (see Non-Patent Document 2, etc.), a method of discovering a double-stranded RNA virus that suppresses violet root rot fungus (scientific name: "*Helicobasidium mompa*") and using an attenuated violet root rot fungal strain incorporating the double-stranded RNA to control violet root rot (see Non-Patent Document 3, Patent Document 3, etc.), etc., have been disclosed.

[Patent Document 1]
Japanese Published Unexamined Patent Application No. 2004-143045
[Patent Document 2]
Japanese Published Unexamined Patent Application No. 2003-250370
[Patent Document 3]
Japanese Published Unexamined Patent Application No. 2001-78752
[Non-Patent Document 1]
C. M. Fauquet, Mary Ann Mayo, J. Maniloff, U. Desselberger, L. A. Ball, "Virus Taxonomy: Classification and Nomenclature of Viruses; Eighth Report Of The International Committee On Taxonomy Of Viruses," Elsevier Academic Press: pp. 591-595.
[Non-Patent Document 2]
Gil H. Choi and Donald L. Nuss, "Hypovirulence of chestnut blight fungus conferred by an infectious viral cDNA." Science. 1992 Aug. 7; 257(5071): 800-3.
[Non-Patent Document 3]
H. Osaki et al, "Detection of Double-Stranded RNA Virus from a Strain of the Violet Root Rot Fungus *Helicobasidium mompa* Tanaka" Virus Genes 25:2, 139-145, 2002.

DISCLOSURE OF THE INVENTION

Problems to be Solved by the Invention

As mentioned above, phytopathogenic fungi have high impacts on quality, yield, etc., of plants and crops. Meanwhile, discoveries of mycoviruses that suppress phytopathogenic fungi have been few and attempts at controlling plant diseases using such mycoviruses have hardly been made. A main object of the present invention is to provide a novel mycovirus that suppresses phytopathogenic fungi and a novel method for controlling plant diseases.

Means for Solving the Problems

The present inventors independently collected naturally-occurring phytopathogenic fungi and searched for mycoviruses that act suppressingly on these fungi. As a result, we have isolated and identified a novel mycovirus exhibiting a phytopathogenic fungus suppressing action and having four types of double-stranded RNA of 2.8 to 3.6 kb and have determined a full-length sequence of the mycovirus.

The present invention thus provides the novel, naturally-occurring mycovirus, isolated by the present inventors, that exhibits the phytopathogenic fungus suppressing action and has the four types of double-stranded RNA of 2.8 to 3.6 kb, and also provides genes thereof, base sequences thereof, nucleic acids having at least a sequence of a specific portion, within the aforementioned sequences, having a specific function, one or a plurality of proteins encoded by the aforementioned sequences, etc.

The mycovirus has a conserved motif of RdRp (RNA-dependent RNA polymerase) contained in the double-stranded RNA sequence, and the RNA base sequence encoding this region is homologous among known Chrysoviridae viruses. The mycovirus is thus presumed to be a novel species of virus classified under Chrysoviridae.

As mentioned above, the present mycovirus exhibits an action of suppressing growth, etc., of phytopathogenic fungi. Thus, for example, by infecting, etc., a host fungus with the mycovirus and making the mycovirus endogenous in the host fungus, an attenuated strain of the phytopathogenic fungus can be prepared.

Or, for example, by adding (by spraying, coating, etc.) a plant disease control agent, containing at least either or both of the mycovirus according to the present invention and the prepared attenuated strain of the phytopathogenic fungus, to a plant (rice, etc.), there is a possibility of being able to control the corresponding plant disease.

Besides the above, the mycovirus according to the present invention has the following characteristics.

Conventionally, a mycovirus is regarded to be transmitted vertically from cell to cell of a host fungus via hyphal fusion and it is considered that a life cycle of a mycovirus does not have a stage where the mycovirus is present outside a host fungus cell. In contrast, by research of the present inventors, it has become known that the mycovirus according to the present invention can be present extracellularly.

Because a host cell can thus be infected with the mycovirus according to the present invention from outside the cell and without depending on hyphal fusion, the mycovirus can infect widely across fungal hosts and strains that differ in conjugation type and can infect host fungi at high efficiency. That is, there is thus a high possibility of achieving attenuation of phytopathogenic fungi and control of plant diseases easily and highly efficiently.

Also, because the mycovirus according to the present invention can be present extracellularly, for example, by culturing a host fungus in a liquid medium and recovering the mycovirus from a supernatant of the culture, the mycovirus can be produced easily and at a comparatively large amount.

Effect(s) of the Invention

The present invention provides a possibility of controlling plant diseases easily and highly efficiently.

BEST MODE(S) FOR CARRYING OUT THE INVENTION

Virus According to the Present Invention

The present invention includes all mycoviruses exhibiting a phytopathogenic fungus suppressing action and having four types of double-stranded RNA of 2.8 to 3.6 kb.

With the present mycovirus, each virus particle has any one of the four types of double-stranded RNA of 2.8 to 3.6 kb, and the mycovirus subsists and repeats generations in a state where virus particles of the four types are present simultaneously. In addition, each of the abovementioned chestnut blight fungus mycovirus and violet root rot fungus mycovirus is made up of a double-stranded RNA of a single component of no less than 12 kb and differs largely in structure from the mycovirus according to the present invention. Therefore, there is a high possibility that the mycovirus according to the present invention is a completely different virus species and there is also a high possibility that a mechanism of attenuation of a host fungus differs greatly as well.

As mentioned above, the mycovirus has the conserved motif of RdRp (RNA-dependent RNA polymerase) contained in the double-stranded RNA sequence, and the base sequence of the RNA encoding this region is homologous among known Chrysoviridae viruses. The mycovirus is thus presumed to be a novel species of virus classified under Chrysoviridae.

Base sequences of the four types of the double-stranded RNA of the mycovirus are indicated by SEQ ID NOS: 1 to 4, and amino acid sequences of proteins encoded by the base sequences are indicated by SEQ ID NOS: 5 to 8.

Although all base sequences shown in the sequence table are indicated as DNA sequences, the sequences according to the present invention includes these sequences and all sequences in the case of RNA (where thymine is replaced by uracil) (the same applies hereinafter).

In regard to the base sequence of the region encoding RdRp (RNA-dependent RNA polymerase), sequence analysis has shown the homology to be 22% and the similarity to be 39% between the mycovirus and Hv145SV, the homology to be 23% and the similarity to be 38% between the mycovirus and PcV, and the homology to be 28% and the similarity to be 45% between the mycovirus and AbV1.

The mycovirus according to the present invention thus includes all viruses for which, with respect to the region encoding RdRP (RNA-dependent RNA polymerase) in the genome of a Chrysoviridae virus (for example, any one of Hv145SV, PcV, and AbV1), the homology is 20% to 100% and the similarity is 40% to 100%. Here "homology" refers to complete matching of base sequences, and "similarity" refers to complete matching of base sequences upon replacement of adenine with guanine or thymine (uracil) with cytosine.

The mycovirus according to the present invention is present endogenously in a predetermined rice blast fungus. The mycovirus can thus be acquired, for example, by separating and recovering the virus from a rice blast fungal strain latently infected by the mycovirus. In addition, the rice blast fungus endogenously containing the mycovirus according to the present invention can be cultured under the same medium and culturing conditions as those of a normal rice blast fungus.

As an example of a mycovirus according to the present invention, for example, MoCV1 (*Magnaporthe oryzae* chrysovirus 1), identified and named by the present inventors, can be cited. This virus is endogenous at least in an "S-0412-II 1a" strain of rice blast fungus (scientific name: "*Magnaporthe oryzae*"). Although depositions of this rice blast fungal strain at the International Patent Organism Depositary of the National Institute of Advanced Industrial Science and Technology and at the Patent Microorganisms Depositary of the National Institute of Technology and Evaluation were requested, the depositions were refused on grounds of endogenously containing a virus. The present fungal strain is preserved at the Laboratory of Plant Pathology, Tokyo University of Agriculture and Technology and can be shared with a third party under conditions of adherence to laws and regulations.

The "S-0412-II 1a" strain of rice blast fungus (scientific name: "*Magnaporthe oryzae*") has been internationally deposited at the international depository in Germany, DSMZ (Deutsche Sammlung con Mikroorganismen and Zellkulturen GmbH, address: Inhoffenstr. 7B D-38124 Braunschweig GERMANY) (date of deposition: Mar. 25, 2008, deposition number: DSM21334). The same strain has also been internationally deposited at the international depository in the USA, ATCC (American Type Culture Collection, address: University Boulevard Manassas, Va. 20110-2209 USA) (date of deposition: May 15, 2008, deposition number: PTA-9137). The country of origin of this fungal strain is Vietnam.

Known methods may be employed to separate and recover the virus. For example, a fungus body may be frozen by liquid nitrogen, etc., fragmented, and suspended in a predetermined buffer solution and thereafter, the virus can be recovered by separating the virus by ultracentrifugation, etc.

Also, as mentioned above, the present virus can be present extracellularly. Thus, for example, a phytopathogenic fungus (a predetermined rice blast fungus, etc.) containing the mycovirus may be cultured in a liquid medium and the virus may be separated and recovered from a supernatant of the culture. The present virus itself can be prepared at any time at the Laboratory of Plant Pathology, Tokyo University of Agriculture and Technology and be shared with a third party.

<Genes, Nucleic Acids, Proteins, Etc., According to the Present Invention>

The present inventors performed sequence analysis and obtained full-length base sequences of one mycovirus according to the present invention (SEQ ID NOS: 1 to 4). Therefore, the present invention thus includes all of: genes of the mycovirus; nucleic acids having the base sequences or portion thereof; proteins encoded by the base sequences, etc.

The present invention includes mycovirus genes having the four types of sequences of SEQ ID NOS: 1 to 4.

The present invention also includes all nucleic acids having all or a portion of the base sequences. The nucleic acid may be double-stranded or single-stranded, and all of DNAs, cDNAs, RNAs, etc., are included.

The present invention also includes all sequences or any sequence of SEQ ID NOS: 1 to 4, sequences of specific portions in the aforementioned sequences having predetermined functions, cDNAs having base sequences equivalent to the aforementioned sequences, recombinant vectors (plasmids, viruses, etc.) incorporating base sequences equivalent to the aforementioned sequences, etc.

As a result of the sequence analysis, it was found that the conserved motif of RdRp (RNA-dependent RNA polymerase) is present in a sequence portion of SEQ ID NO: 1 and that a sequence portion of SEQ ID NO: 3 is homologous to a double-stranded RNA fragment of a La France disease virus. Thus, in accordance with purpose or application, a nucleic acid, a recombinant vector, etc., having at least these sequence portions as specific portions having predetermined functions may be prepared and used, for example.

In addition, the nucleic acids (or genes) according to the present invention also broadly include nucleic acids homologous to the aforementioned base sequences, for example, nucleic acids that hybridize under stringent conditions with nucleic acids made up of base sequences complementary to the base sequences and exhibits rice blast fungus suppressing action. The stringent conditions here, such as a Tm value of a double-stranded nucleic acid, can be acquired by known arts.

The present invention also includes all proteins encoded by the aforementioned mycovirus genes and nucleic acids. Amino acid sequences of proteins according to the present invention are indicated by SEQ ID NOS: 5 to 8.

Respectively speaking, SEQ ID NO: 5 is an amino acid sequence of an open reading frame in the base sequence indicated by SEQ ID NO: 1, SEQ ID NO: 6 is an amino acid sequence of an open reading frame in the base sequence indicated by SEQ ID NO: 2, SEQ ID NO: 7 is an amino acid sequence of an open reading frame in the base sequence indicated by SEQ ID NO: 3, and SEQ ID NO: 8 is an amino acid sequence of an open reading frame in the base sequence indicated by SEQ ID NO: 4.

All proteins homologous to and maintaining the functions of the proteins having any one of the amino acid sequences of SEQ ID NOS: 5 to 8 are included among the proteins according to the present invention.

For example, by incorporating an abovementioned nucleic acid in a recombinant vector and subjecting the host to forced expression, the corresponding protein can be produced in large quantities. It is considered that coliform bacteria, yeasts, cultured cells, and other known hosts can be used as the host. In consideration that the mycovirus infects fungus and that yeasts have a high proliferation ability and can be used comparatively simply, yeasts are possibly optimal hosts. It is also considered in regard to recombinant vectors that a known vector can be used.

There is a possibility that by using a plurality of vectors incorporating any one of SEQ ID NOS: 1 to 4 and making a plurality of the four types of genes be coexpressed, the mycovirus can be reconstituted. It is considered that a known host and a known recombinant vector can be used in this case as well, and there is a possibility that yeasts are optimal in that a plurality of vectors can be introduced simultaneously.

<Attenuated Phytopathogenic Fungal Strain>

Attenuated phytopathogenic fungal strains according to the present invention include all attenuated strains endogenously incorporating the mycovirus according to the present invention. That is, for example, both rice blast fungus and other strains already containing the mycovirus endogenously and phytopathogenic fungal strains infected by the mycovirus are included.

As a method for infecting, etc., a phytopathogenic fungus with a mycovirus, for example, there is a method of infecting a host fungus during hyphal fusion as is done conventionally. Also, because as mentioned above, the mycovirus according to the present invention can be present extracellularly, for example, it can be made to infect a host fungus directly from outside the cell.

The abovementioned S-0412-II 1a strain can be cited as an example of the attenuated phytopathogenic fungal strain. This fungal strain is a strain of rice blast fungus infected by the mycovirus according to the present invention. Therefore, its morphological characteristics, culturing characteristics, spore formation, and physiological and chemotaxonomic characteristics are thus basically the same as those of known rice blast fungus. However, in comparison to normal rice blast fungus, the present fungal strain is slower in growth, has hyphae that grow non-concentrically, and is pigmented non-uniformly. Also, abnormal development of aerial hyphae is seen and sector formation and lysis are observed.

<Plant Disease Control Agent>

Plant disease control agents according to the present invention include all plant disease control agents containing at least one of either the mycovirus according to the present invention or the attenuated phytopathogenic fungal strain according to the present invention. In addition, both the mycovirus and attenuated phytopathogenic fungal strain may be contained and other components may be contained as well.

As the other components, for example, a predetermined carrier, binder, thickener, fixing agent, antiseptic/antifungal agent, solvent, stabilizer, antioxidant, antiultraviolet agent, anticrystallization agent, antifoam agent, property improver, colorant, etc., may be contained. Also, other agricultural chemical components, such as a miticide, nematicide, bactericide, antiviral agent, attractant, herbicide, plant growth regulator, synergist, etc., may be contained.

As a carrier, for example, either or both of a solid carrier and a liquid carrier may be used. Powders of plant and animal origin, such as starch, activated carbon, soy flour, flour, wood flour, fish flour, powder milk, etc., and mineral powders, such as talc, kaolin, bentonite, zeolite, diatomaceous earth, white carbon, clay, alumina, calcium carbonate, potassium chloride, ammonium sulfate, etc., can be cited as examples of a solid carrier. Water, alcohols, such as isopropyl alcohol, ethylene glycol, etc., ketones, such as cyclohexanone, methyl ethyl ketone, etc., ethers, such as propylene glycol monomethyl ether, diethylene glycol mono-n-butyl ether, etc., aliphatic hydrocarbons, such as kerosene, light oil, etc., aromatic hydrocarbons, such as xylene, trimethylbenzene, tetramethylbenzene, methylnaphthalene, solvent naphtha, etc., amides, such as N-methyl-2-pyrrolidone, etc., esters, such as fatty acid glycerin esters, etc., and vegetable oils, such as soy oil, rape oil, etc., can be cited as examples of a liquid carrier.

Starch, dextrin, cellulose, methylcellulose, ethylcellulose, carboxymethylcellulose, hydroxyethylcellulose, hydroxypropylcellulose, hydroxypropylmethylcellulose, carboxymethyl starch, pullulan, sodium alginate, ammonium alginate, alginic acid propylene glycol ester, guar gum, locust bean gum, gum arabic, xanthan gum, gelatin, casein, polyvinyl alcohol, polyethylene oxide, polyethylene glycol, ethylene/propylene block copolymer, sodium polyacrylate, polyvinylpyrrolidone, etc., can be cited examples of a binder, thickener, or fixing agent.

The present control agent is not particularly restricted in dosage form. For example, forms, such as emulsion formulation, suspension formulation, powder formulation, granular formulation, tablet formulation, water-dispersible formulation, water-soluble formulation, liquid formulation, flowable formulation, granular water-dispersible formulation, aerosol formulation, paste formulation, oil formulation, latex formulation, etc., can be applied.

<Method for Producing Phytopathogenic Fungus Suppressing Mycovirus>

Methods for producing the phytopathogenic fungus suppressing mycovirus according to the present invention include all methods that include at least procedures of culturing a phytopathogenic fungus containing the mycovirus in a liquid medium, etc., and recovering the mycovirus from a supernatant of the culture.

As mentioned above, the mycovirus according to the present invention can be present extracellularly of the host fungus. Thus, for example, by culturing a phytopathogenic fungus, infected by the mycovirus, in a liquid medium, etc., separating the virus from the fungal body by centrifugation, and thereafter separating and recovering the virus from the culture supernatant, the virus can be recovered easily and at a comparatively large amount.

However, the mycovirus according to the present invention is not narrowly restricted to that which is obtained by the above production method. Thus, for example, mycoviruses separated and recovered from rice blast fungi containing mycoviruses endogenously are broadly included in the present invention.

<Method for Attenuating Phytopathogenic Fungus>

As mentioned above, for example, by making the mycovirus according to the present invention infect, etc., a specific pathogenic fungus, growth, etc., of the host fungus can be suppressed and the fungus can be attenuated. As methods for infecting with the mycovirus, the same methods as those mentioned above may be adopted.

<Method for Controlling Plant Disease>

Methods for controlling plant disease according to the present invention include all methods that include at least a step of adding the abovementioned rice blast control agent to a specific plant (such as rice, etc.).

As methods for adding the control agent to a plant, methods of coating top surfaces or rear surfaces of leaves with the control agent, methods of attaching the control agent to top surfaces or rear surfaces of leaves using a predetermined carrier, etc., methods of spraying or supplying the control agent onto leaves, etc., can be cited as examples.

A coating amount or spraying amount of the control agent may be selected as suited according to various conditions, such as concentrations of effective components, form of preparation, type of targeted disease or crop, degree of damage due to disease, location of application, method of application, timing of application, usage amounts and types of chemicals, fertilizers, etc., mixed or used in combination, etc.

For example, there is a possibility that a plant disease can be controlled by spraying or supplying a liquid, containing conidia of an attenuated rice blast fungal strain and adjusted to $1\times10^3$ to $1\times10^{10}$ conidia/mL, at an amount of 1 to 1,000 mL per leaf or by coating or attaching conidia of an attenuated rice blast fungal strain to top surfaces or rear surfaces of leaves at an amount of $1\times10^3$ to $1\times10^{10}$ conidia per 1 $mm^2$ of leaf.

There is a possibility that the present invention can be applied to all plant diseases for which a fungus is a main cause. As plant diseases for which there is a possibility of application, the following can be cited as examples (however, the present invention is not limited to these).

Examples of plant diseases of plants of the family Poaceae include rice blast (causative fungus: "*Magnaporthe oryzae*"), rice brown spot (causative fungus: "*Cochliobolus miyabeanus*"), sheath blight (causative fungus: "*Thanatephorus cucumeris*"), bakanae disease (causative fungus: "*Gibberella fujikuroi*"), seedling blight (causative fungi: "*Fusarium* fungi," "*Rhizopus* fungi," "*Pythium* fungi," "*Trichoderma viride*"), false smut (causative fungus: "*Claviceps virens*"), fusarium blight of wheat (causative fungi: "*Gibberella zeae,*" "*Fusarium avenaceum,*" "*Fusarium culmorum,*" "*Monographella nivale*"), snow mold (causative fungi: "*Pythium* fungi," "*Typhula* fungi," "*Monographella nivalis,*" "*Myriosclerotinia borealis*"), loose smut (causative fungus: "*Ustilago nuda*"), stinking smut (causative fungus: "*Tilletia controversa*"), eye spot (causative fungus: "*Pseudocercosporella herpotrichoides*"), leaf blotch (causative fungus: "*Septoria trifler*"), glume blotch (causative fungus: "*Phaeosphaeria nodorum*"), and powdery mildew (causative fungus: "*Blumeria graminis*").

Examples of other plant diseases include melanose (causative fungus: "*Diaporthe citri*"), melanose-like blemish (causative fungi: "*Diaporthe medusa,*" "*Alternaria citri*"), scab (causative fungus: "*Elsinoe fawcettii*"), brown rot (causative fungus: "*Phytophthora citrophthra*"), green mold (causative fungus: "*Penicillium digitatum*"), and blue mold (causative fungus: "*Penicillium italicum*") of citruses, blossom blight (causative fungus: "*Monilinia mali*"), scab (causative fungus: "*Venturia inaequalis*"), alternaria blotch (causative fungus: "*Alternaria mali*"), fruit spot (causative fungus:

"*Mycosphaerella pomi*"), sooty blotch (causative fungus: "*Gloeodes pomigena*"), fly speck (causative fungus: "*Zygophiala jamaicensis*"), ring rot (causative fungus: "*Botryosphaeria berengeriana*"), blotch (causative fungus: "*Diplocarpon mali*"), rust (causative fungus: "*Gymnosporangium yamadae*"), and valsa canker (causative fungus: "*Valsa ceratosperma*") of apple, scab (causative fungus: "*Venturia nashicola*"), rust (causative fungus: "*Gymnosporangium asiaticum*"), ring rot (causative fungus: "*Botryosphaeria berengeriana*"), and phomopsis canker (causative fungus: "*Phomopsis fukushii*") of pear, leaf curl (causative fungus: "*Taphrina deformans*"), brown rot (causative fungi: "*Monilinia fructicola*," "*Monilinia fructigena*"), scab (causative fungus: "*Cladosporium carpophilum*"), and phomopsis rot (causative fungus: "*Phomopsis sp.*") of peach, brown rot (causative fungi: "*Monilinia fructicola*," "*Monilinia fructigena*") and young fruit rot (causative fungus: "*Monilinia kusanoi*") of cherry, scab (causative fungus: "*Cladosporium carpophilum*") of Japanese apricot, anthracnose (causative fungus: "*Elsinoe ampelina*"), ripe rot (causative fungi: "*Colletotrichum acutatum*," "*Glomerella cingulata*"), leaf blight (causative fungus: "*Pseudocercospora vitis*"), and dead arm (causative fungus: "*Phomopsis viticola*") of grape, angular leaf spot (causative fungus: "*Cercospora kaki*") and circular leaf spot (causative fungus: "*Mycosphaerella nawae*") of persimmon, gray blight (causative fungi: "*Pestalotiopsis longiseta*," "*Pestalotiopsis theae*"), brown round spot (causative fungi: "*Pseudocercospora ocellata*," "*Cercospora chaae*"), blister blight (causative fungus: "*Exobasidium vexans*"), and net blister blight (causative fungus: "*Exobasidium reticulatum*") of tea, gummy stem blight (causative fungus: "*Mycosphaerella melonis*"), fusarium wilt (causative fungus: "*Fusarium oxysporum*"), scab (causative fungus: "*Cladosporium cucumerinum*"), and corynespora leaf spot (causative fungus: "*Corynespora cassiicola*") of cucurbitaceous fruits, leaf mold (causative fungus: "*Fulvia fulva*"), and early blight (causative fungus: "*Alternaria solani*") of tomato, brown spot (causative fungus: "*Phomopsis vexans*") and leaf mold (causative fungus: "*Mycovellosiella nattrassii*") of eggplant, white rust (causative fungus: "*Albugo macrospora*"), and white spot (causative fungi: "*Cercosporella brassicae*," "*Pseudocercosporella capsellae*") of brassicaceous vegetables, gray mold (causative fungus: "*Botrytis allii*") of onion, leaf spot (causative fungus: "*Mycosphaerella fragariae*") of strawberry, early blight (causative fungus: "*Alternaria solani*") of potato, stem rot (causative fungus: "*Phytophthora sojae*") and purple stain (causative fungus: "*Cercospora kikuchii*") of soy, stem rot (causative fungus: "*Phytophthora vignae*") of adzuki bean, brown leaf spot (causative fungus: "*Mycosphaerella arachidis*") of peanut, cercospora leaf spot (causative fungus: "*Cercospora beticola*") and leaf blight (causative fungus: "*Thanatephorus cucumeris*") of sugar beet, curvularia leaf blight (causative fungus: "*Curvularia* fungus"), dollar spot (causative fungus: "*Sclerotinia homoeocarpa*"), and *Helminthosporium* leaf blight (causative fungus: "*Cochliobolus* fungus") of lawn grass, black spot (causative fungus: "*Diplocarpon rosae*") of rose, white rust (causative fungus: "*Puccinia horiana*") of chrysanthemum, downy mildew (causative fungi: "*Peronospora* fungus," "*Pseudoperonospora* fungus," "*Plasmopara* fungus," "*Bremia* fungus"), blight (causative fungus: "*Phytophthora* fungus"), powdery mildew (causative fungi: "*Erysiphe* fungus," "*Blumeria* fungus," "*Sphaerotheca* fungus," "*Podosphaerea* fungus," "*Phyllactinia* fungus," "*Uncinula* fungus," "*Oidiopsis* fungus"), rust (causative fungi: "*Puccinia* fungus," "*Uromyces* fungus," "*Physopella* fungus"), leaf spot (causative fungus: "*Alternaria* fungus"), gray mold (causative fungus: "*Botrytis cinerea*"), sclerotina rot (causative fungus: "*Sclerotinia sclerotiorum*"), white root rot (causative fungus: "*Rosellinia necatrix*"), violet root rot (causative fungus: "*Helicobasidium mompa*"), southern blight (causative fungus: "*Sclerotium rolfsii*") of various crops, and various other soil diseases (causative fungus: "*Fusarium* fungus," "*Rhizoctonia* fungus," "*Pythium* fungus," "*Aphanomyces* fungus," "*Phoma* fungus," "*Verticillium* fungus," "*Plasmodiophora brassicae*," etc.).

EXAMPLE 1

In Example 1, detection of endogenous double-stranded RNAs from 57 rice blast fungal strains was attempted.

First, respective fungal bodies of 57 independently collected strains of rice blast fungus were milled, and after extracting nucleic acids by a phenol-SDS method, DNAs and single-stranded nucleic acids were selectively digested by DNase 1 and S1 nuclease to obtain a solution of double-stranded RNAs endogenous to the fungal bodies. Electrophoresis using a 1% agarose gel was performed at 20V for 18 hours and staining by ethidium bromide was performed.

As a result, double-stranded RNA bands were detected in 11 of the 57 strains. Of these, bands of four components were detected at 2.8 to 3.6 kb in 7 strains, bands of three components were detected at 1.0 to 2.6 kb in 3 strains, and bands of eight components were detected at 1.0 to 3.6 kb in 1 strain.

FIG. 1 is an electrophoresis photograph of results of double-stranded RNA detection for 9 of the 57 rice blast fungal strains. In FIG. 1, a DNA marker is applied in lane 1, and samples prepared from the fungal bodies were applied in lanes 2 to 10. In FIG. 1, whereas a double-stranded RNA band was not detected in lanes 6 and 8, bands of four components were detected at 2.8 to 3.6 kB in lanes 2, 3, 4, 5, and 10, bands of three components were detected at 1.0 to 2.6 kb in lane 7, and bands of eight components were detected at 1.0 to 3.6 kb in lane 9.

In the above experimental results, in consideration that a plurality of bands were detected from single strains and in consideration of the lengths of the double-stranded RNAs, there is a high possibility that the double-stranded RNAs detected from the 11 rice blast fungal strains are double-stranded RNAs making up a mycovirus. That is, the results of the present example suggest that a novel mycovirus is endogenous in these rice blast fungal strains.

EXAMPLE 2

Based on the results of Example 1, growth rates of strains containing the double-stranded RNAs endogenously and strains not containing any double-stranded RNAs endogenously were compared in Example 2.

Fungal strains with which endogenous double-stranded RNAs were detected and fungal strains with which endogenous double-stranded RNAs were not detected in Example 1 were cultured in a PDA medium and colonies were observed after 6 days and after 10 days from the start of culturing.

As a result, with fungal strains with which endogenous double-stranded RNAs were not detected, hyphae grew in concentric circles and pigmentation was uniform. On the other hand, with fungal strains with which endogenous double-stranded RNAs were detected, growth was slower than fungal strains with which RNAs were not detected, hyphae grew non-concentrically, and pigmentation was non-uniform. Also, abnormal development of aerial hyphae was seen and sector formation and lysis were observed.

That is, with the fungal strains endogenously containing double-stranded RNAs, suppression of growth was observed in comparison to the fungal strains in which double-stranded RNAs were not endogenous. These experimental results suggest that the double-stranded RNAs (mycovirus) obtained in Example 1 are growth suppression factors (attenuation factors) of rice blast fungus.

EXAMPLE 3

In Example 3, preparation of mycovirus-cured strains by treatment of fungal strains endogenously containing the double-stranded RNAs with low-concentration cycloheximide (protein synthesis inhibitor) was attempted.

YG plates with 0.25 to 0.50 μg/ml of cycloheximide added were prepared and the strains cultured in Example 2 (strains with which endogenous double-stranded RNAs were detected) were transferred to these plates. Of the formed colonies, portions that recovered to normal growth were transferred to separate YG plates to obtain cycloheximide-treated fungal strains. As a result, the cycloheximide-treated fungal strains exhibited better growth than normal rice blast fungal strains.

Next, from the cycloheximide-treated fungal strains obtained, extraction of double-stranded RNA and detection of double-stranded RNA bands by electrophoresis were attempted using the same methods as those of Example 1. As a result, bands of double-stranded RNA were not detected from the cycloheximide-treated fungal strains.

Mycovirus-cured fungal strains were also prepared by a different method and subject to the same experiment.

After the fungal strains cultured in Example 2 were grown for approximately 1 to 3 weeks on a PDA medium or an oatmeal medium, conidia were isolated, the conidia were transferred one by one to a new PDA medium, and fungal colonies from which the mycovirus was removed were selected as mycovirus-cured fungal strains.

As a result, even with these cured fungal strains, growth became clearly better than that of virus-carrying strains. Also, as a result of attempting detection of double-stranded RNA bands by electrophoresis in the same manner as described above, double-stranded RNA bands were not detected from the cured fungal strains.

These results indicate that the double-stranded RNAs contained endogenously in the rice blast fungus are those of a mycovirus and that this mycovirus is a growth suppression factor of rice blast fungus.

EXAMPLE 4

In Example 4, it was examined whether or not the mycovirus according to the present invention is present outside the fungal body of rice blast fungus.

Of the fungal strains with which endogenous double-stranded RNA bands of four components were detected at 2.8 to 3.6 kb in Example 1, three strains were transferred to and cultured in liquid media, and thereafter the culture solutions were centrifuged and culture supernatants were recovered. Next, the culture supernatants obtained were electrophoresed in 1% agarose gel at 20V for 18 hours and stained by ethidium bromide.

As a result, double-stranded RNA bands at the same positions as the fungal endogenous double-stranded RNAs were detected from the culture supernatants of these fungal strains as well.

This result indicates that the mycovirus according to the present invention can be present not only inside the fungal body of rice blast fungus but also outside the fungal body.

EXAMPLE 5

In Example 5, it was examined whether or not the mycovirus present outside the fungal body has an infectious ability with respect to normal strains (strains not carrying the mycovirus).

First, the fungal strains with which endogenous double-stranded RNA bands of four or more components were detected at 2.8 to 3.6 kb in Example 1 were transferred to liquid media, and after culturing for 4 weeks, the culture solutions were centrifuged and culture supernatants were recovered. As a result of electrophoresing the culture supernatants in 1% agarose gel in the same manner as in Example 4, the double-stranded RNA bands were observed. The culture supernatants obtained were filtration sterilized using 0.22 μL filters.

Next, 50 ml of YG medium were placed in a 100 ml flask, a normal strain of rice blast fungus (strain not carrying the mycovirus) was inoculated therein, and after culturing for 3 days, 500 μL of the culture supernatant obtained were added and growth of the fungal body was observed.

As a result, on the third day of observation, whereas with a strain to which the culture supernatant was not added, hypha tips grew straightly, indicating normal growth, with a strain to which the culture supernatant was added, hypha tips did not extend much and were in an entangled state.

This result is considered to be due to infection and growth suppression of the normal rice blast fungus by the mycovirus present in the culture supernatant. That is, the present experimental results suggest that the mycovirus present outside the fungal body has an infectious ability with respect to a normal fungal strain.

EXAMPLE 6

In Example 6, conidia count measurements were performed on rice blast fungus strains infected with the mycovirus.

The fungal strains with which endogenous double-stranded RNA bands of four or more components were detected at 2.8 to 3.6 kb in Example 1 were transferred to YG plates, and after culturing for 2 weeks, fungal bodies were extracted and collected using a 4 mm cork borer.

5% glycerol, and then, the collected fungal body were placed in a 1.5 ml tube and mixing and suspending were performed for 5 minutes. The number of conidia present in the suspension was then counted using a blood cell counting chamber.

As a result, whereas with the normal strain of rice blast fungus (control, strain not carrying the mycovirus), the conidia count was $33 \times 10^4$ conidia/mL, the conidia count was no more than $1 \times 10^4$ conidia/ml with rice blast fungal strains endogenously containing the mycovirus.

This result indicates that the mycovirus according to the present invention suppresses conidia formation by host fungi. That is, it is suggested that the present invention has a possibility of suppressing proliferation of phytopathogenic fungi and being able to suppress propagation and spreading of infection of the fungi.

EXAMPLE 7

In Example 7, the base sequences of the double-stranded RNAs extracted from the rice blast fungus were analyzed.

(1) Extraction and Purification of Double-Stranded RNAs

First, the double-stranded RNAs were extracted and purified by the following procedure.

One of the fungal strains with which double-stranded RNAs were detected in Example 1 was frozen by liquid nitrogen and thereafter milled, and 1 ml of an extraction buffer (2×STE, 1% SDS, 10 mM β-mercaptoethanol) was added per 0.1 g of fungal body. PCI (50% phenol, 48% chloroform, 2% isoamyl alcohol) of an amount equivalent to the extraction buffer was then added to the solution, and the mixture was stirred well at room temperature for 30 minutes and then centrifuged (8,000 rpm, for 20 minutes, room temperature), and a supernatant (aqueous phase) was collected. An equivalent amount of 100% ethanol was added to the collected supernatant (50% ethanol/1×STE solution as the final concentration) to perform ethanol precipitation.

The precipitate (nucleic acid) obtained was dissolved in a 17.5% ethanol/1×STE solution and, after heat treating at 65° C. for 10 minutes, was cooled rapidly in ice, and after centrifuging (8,000 rpm, for 10 minutes, 4° C.), a supernatant was collected. A fibrous cellulose filler (trade name: "CF11," made by Whatman Inc.) was added to the supernatant, and after stirring for 30 to 60 minutes under a 4° C. condition, the supernatant was filled in a column (diameter: 1.5 cm; height: 12 cm).

Next, the 17.5% ethanol/1×STE solution was supplied to the column and after eliminating a non-adsorbed fraction, a 1×STE solution was added to elute and recover an adsorbed fraction. To eliminate DNA mixed in the eluted fraction, 25 U of DNase 1 (made by Takara Bio Inc.) were added and after letting react for 30 minutes at 37° C., ethanol precipitation was performed and the targeted double-stranded RNAs were obtained.

(2) cDNA Cloning cDNA was synthesized using the obtained double-stranded RNAs as templates and thereafter, cDNA cloning was performed.

From the obtained double-stranded RNAs, first strand cDNAs were synthesized using Random Primer and SuperScript III reverse transcriptase (made by Invitrogen Corp.; the same applies hereinafter). Then, after treatment by RNase H, second strand cDNAs were synthesized using DNA polymerase I. After terminal blunting the synthesized double-stranded cDNAs by T4 DNA polymerase, purification was performed using a QIAquick PCR Purification Kit (made by Qiagen N. V.; the same applies hereinafter).

Then, after performing terminal phosphorylation, the cDNAs were incorporated in pUC19 plasmid vectors (made by Takara Bio Inc.; the same applies hereinafter), the recombinant vectors were transformed into *Escherichia coli*, and clones of the respective cDNA were thereby obtained. The respective cDNA clones were then subject to sequence measurement.

As a result of preparing coding sequences based on the respective base sequence information obtained, substantially full-length base sequences were acquired for the four types of double-stranded RNAs present in the fungal body.

(3) Analysis of Both Terminal Sequences by a 5'-RACE Method

In continuation, gene-specific antisense primers were synthesized based on the sequence information, double-stranded RNAs were extracted and purified from the fungal body by the same procedure as described above, cDNAs were synthesized using the SuperScript III reverse transcriptase and the primers and treated with RNase H to obtain single-stranded first strand cDNAs.

Then, using terminal deoxynucleotidyl transferase (made by Takara Bio Inc.) deoxycytosine homopolymer was added as anchor sequences to the single-stranded cDNAs. Adapter primers with deoxyguanine homopolymer attached were then synthesized, gene-specific antisense primers, and portions sandwiched by the two primers were amplified by a PCR method to synthesize cDNAs.

Next, the cDNAs were terminal blunted by T4 DNA polymerase, purified using the QIAquick PCR Purification Kit, and then after performing terminal phosphorylation, the cDNAs were incorporated in pUC19 plasmid vectors, the recombinant vectors were transformed into *Escherichia coli*, and clones of the respective cDNAs were thereby obtained. The respective cDNA clones were then subject to sequence measurement.

By the above procedure, the full-length sequences of the genetic information of the novel mycovirus were obtained. This mycovirus is made up of four types of double-stranded RNAs. The sequences of the respective double-stranded RNAs are indicated by SEQ ID NOS: 1 to 4. Because the sequence measurements were made upon replacing the double-stranded RNAs by cDNAs, "uracil" is replaced by "thymine" in the sequence table.

As a result of analysis of the base sequences obtained, it was found that a conserved motif of RdRp (RNA-dependent RNA polymerase), present in totiviruses and related viruses, etc., is included in the RNA sequence indicated by SEQ ID NO: 1. It was also found that a region homologous to an L3 double-stranded RNA fragment of a La France disease virus is included in the RNA sequence indicated by SEQ ID NO: 3.

These results indicate that the four types of double-stranded RNAs according to the present invention make up the genetic information of the novel mycovirus.

EXAMPLE 8

In Example 8, biochemical characteristics of virus particles of the mycovirus according to the present invention were analyzed.

The S-0412-II 1a rice blast fungal strain was frozen by liquid nitrogen and milled by a mortar. 0.1 M phosphate buffer (pH 7.0) of 4 to 6 times the sample amount was then added to the sample and stirring by a mixer was performed. Then, upon adding butanol/chloroform (volume ratio: 1:1) of 40% the volume of the phosphate buffer, the mixture was stirred for 30 minutes and centrifuged (8,000×g, for 10 minutes), the supernatant was recovered, and this operation was repeated several times.

Next, polyethylene glycol (average molecular weight: 6,000) for achieving a final concentration of 8% and sodium chloride for achieving a final concentration of 1% was then added to and dissolved in the supernatant, and upon leaving for 3 hours at 4° C. to make the viruses aggregate mutually, centrifugation (12,000×g, for 20 minutes) was performed to obtain a virus precipitate aggregated by the polyethylene glycol.

The virus precipitate was then dissolved in an appropriate amount of 0.05 M phosphate buffer (pH 7.0), undissolved impurities were eliminated by centrifugation (6,000×g, for 5 minutes), and the supernatant was recovered.

20% sucrose was then dispensed as a cushion to a height of approximately 1 cm from a bottom of a centrifuge tube, the recovered supernatant was overlaid, ultracentrifugation (100,000×g, for 2 hours) was performed, and the precipitate was dissolved in a small amount of 0.05 M phosphate buffer (pH 7.0) as a partially purified virus preparation.

A portion of the virus preparation was subject to SDS-PAGE (7.5% gel, tris-glycine bugger (pH 8.8), 20 mA, for 90 minutes) and stained by CBB (Coomassie brilliant blue) to perform molecular weight analysis of a principal component of virus protein (coat protein).

As a result, a band of virus particle derived protein was detected at a size of approximately 70 kDa.

Then, by the SDS-phenol method, nucleic acid extraction was performed from the component with which the 70 kDa protein is detected. As a result, double-stranded RNAs of four components of 2.8 to 3.6 kbp were detected.

By the present example, presence of virus particles of the mycovirus according to the present invention was confirmed.

EXAMPLE 9

In Example 9, whether or not the present invention is effective for control of a phytopathogenic fungus was examined by a spray inoculation method.

The S-0412-II 1a rice blast fungal strain was inoculated into an oatmeal medium plate and cultured indoors at 25° C. If conidia were not formed adequately on the 15th day after inoculation, approximately 2 mL of sterilized distilled water were poured on the plate, the medium surface was rubbed with a brush to remove aerial hyphae, the plate was placed under a black light for 3 days to induce conidia formation, approximately 1 mL of sterilized distilled water were poured, and the medium surface was rubbed again by a brush to recover conidia along with aerial hyphae to obtain a conidia-containing solution. If conidia were adequately formed on the 15th day after inoculation, approximately 2 mL of sterilized distilled water were poured on the plate, and the medium surface was rubbed with a brush, and recover conidia along with aerial hyphae to obtain a conidia-containing solution. As a control, a completely mycovirus-cured strain of the rice blast fungus was prepared by the same procedure as Example 3, and the conidia-containing solutions was obtained by the same procedure from this fungus.

The conidia-containing solutions were then filtered through Kimwipe or gauze, adjusted to a conidia concentration of $2 \times 10^6$ conidia/mL, and 0.02% (v/v) Tween 20 was added to prepare conidia suspensions.

Next, the conidia suspensions were uniformly sprayed using a nozzle onto rice seedlings (seedlings of 2 to 3 weeks from seeding of a variety selected appropriately in consideration of true rice blast resistance phenotype and fungal race), and after leaving still the plant bodies in an inoculation box at 26° C. and 100% relative humidity for 24 hours, the pots were transferred into a greenhouse with the room temperature being maintained at 23° C. to 30° C. and grown for 7 days after spray inoculation. On the 7th day after spray inoculation, a number per fixed leaf area of disease lesions that have become 3 to 4 mm in size was measured.

The results are shown in FIG. 2. FIG. 2 is a graph showing the number of disease lesions on leaves inoculated by the rice blast fungus. In the figure, the vertical axis indicates the number of lesions on leaves inoculated by the rice blast fungus. In the figure, "Infected strains" indicates the number of lesions in the case of spraying the conidia suspension prepared from the rice blast fungus infected with the mycovirus according to the present invention, and "Completely cured strains" indicates the number of lesions in the case of spraying the conidia suspension prepared from the completely mycovirus-cured strains of the rice blast fungus (control).

As shown in FIG. 2, in the case of spraying the conidia suspension prepared from the rice blast fungus infected with the mycovirus according to the present invention, the number of lesions is significantly decreased in comparison to the control. This indicates that the present invention is effective for control of the phytopathogenic fungus.

EXAMPLE 10

In Example 10, whether or not the present invention is effective for control of a phytopathogenic fungus was examined by a punch inoculation method.

Conidia suspensions were prepared by the same procedure as Example 9, the suspensions were deposited on 3% plain agar films, and the agar films were cut to approximately 2 mm square to prepare agar pieces. Fourth leaves of rice grown in a greenhouse at 23° C. to 30° C. were punched by an inoculation punch to form wet wounds, the agar pieces were placed on the wounded portions, and after leaving still the plant bodies in an inoculation box at 26° C. and 100% relative humidity for 24 hours, the pots were transferred into a greenhouse with the room temperature being maintained at 23° C. to 30° C. and grown for 14 days after inoculation. On the 14th day after inoculation, sizes of lesions were measured.

As a result, in comparison to the control, the lesion sizes were significantly smaller in the case of inoculating the conidia suspension prepared from the rice blast fungus infected with the mycovirus according to the present invention. As with Example 9, this result indicates that the present invention is effective for control of the phytopathogenic fungus.

EXAMPLE 11

In Example 11, virus particles present outside the fungal body were identified using an electron microscope.

The S-0412-II 1a rice blast fungal strain was cultured in the YG medium (yeast extract: 0.5%; glucose: 2%) and virus particles were isolated from the culture supernatant. The culture supernatant was centrifuged (10,000×g, for 5 minutes) and the resulting supernatant was ultracentrifuged (100,000× g, for 30 minutes) to obtain a precipitate containing the virus particles. The precipitate was dissolved in 0.05 M phosphate buffer (pH 7.0), negative stained using phosphotungstic acid or uranium acetate, and observed by an electron microscope (magnification: ×20,000 to 40,000).

The result is shown in FIG. 3. FIG. 3 is an electron micrograph of virus particles obtained from the culture supernatant of the S-0412-II 1a rice blast fungal strain. As shown in FIG. 3, the virus particles of the mycovirus according to the present invention could be identified by use of the electron microscope. The virus particles have a regular hexagonal shape of approximately 30 to 40 nm and were covered by an envelope-like structure.

SEQUENCE LISTING

<160> NUMBER OF SEQ ID NOS: 8

Figure 1:
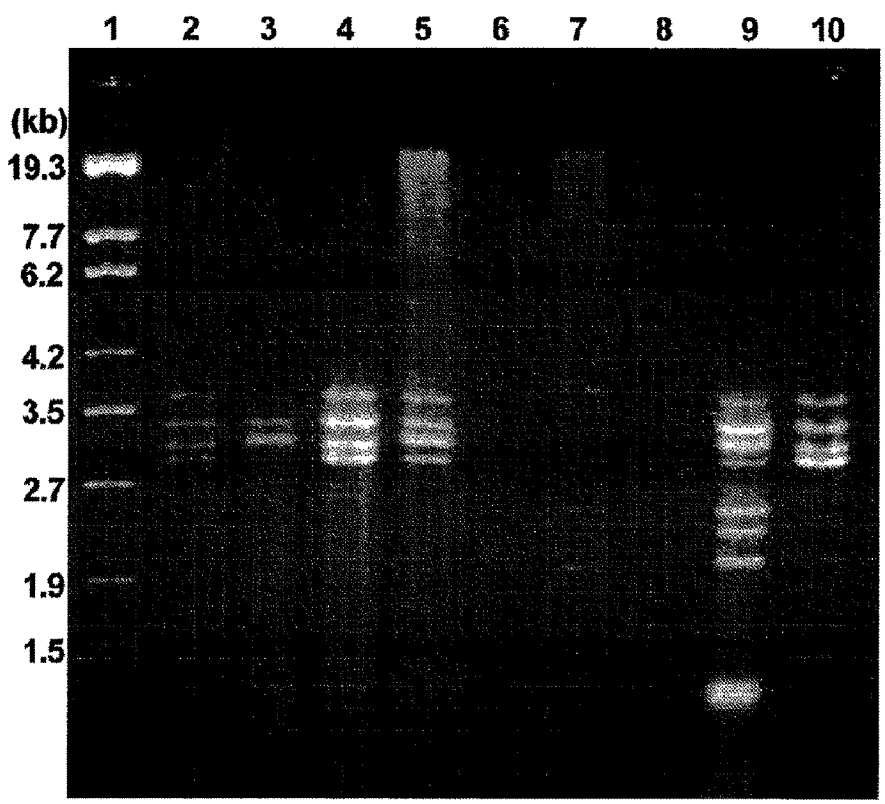
FIG. 1 is an electrophoresis photograph of double-stranded RNA detection results obtained in Example 1 for 9 strains of 57 rice blast fungal strains.
Figure 2:
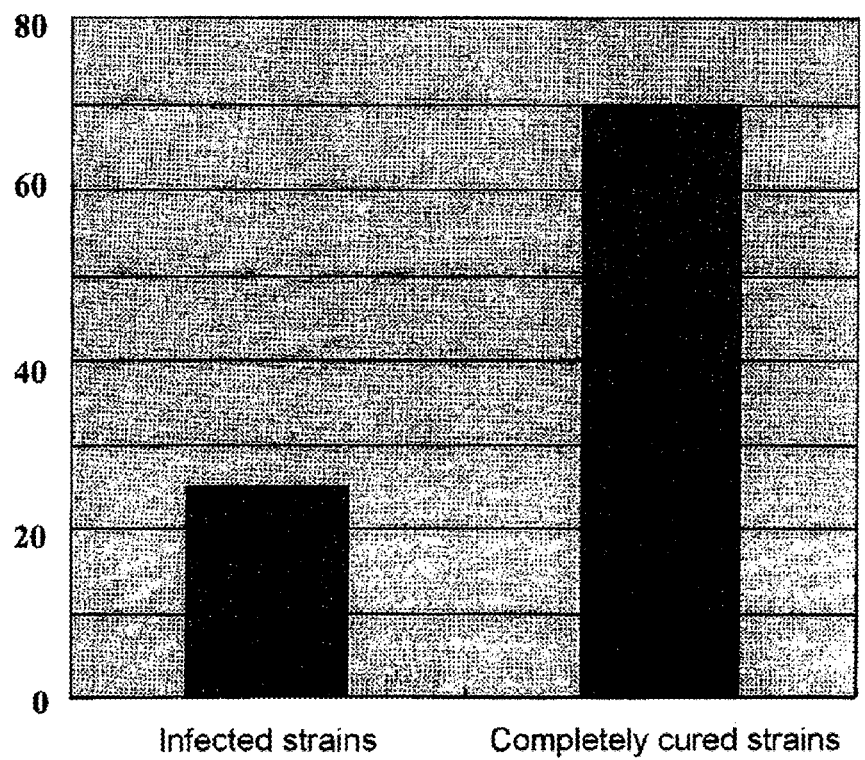
FIG. 2 is a graph of numbers of lesions in leaves inoculated by rice blast fungi in Example 9.
Figure 3:
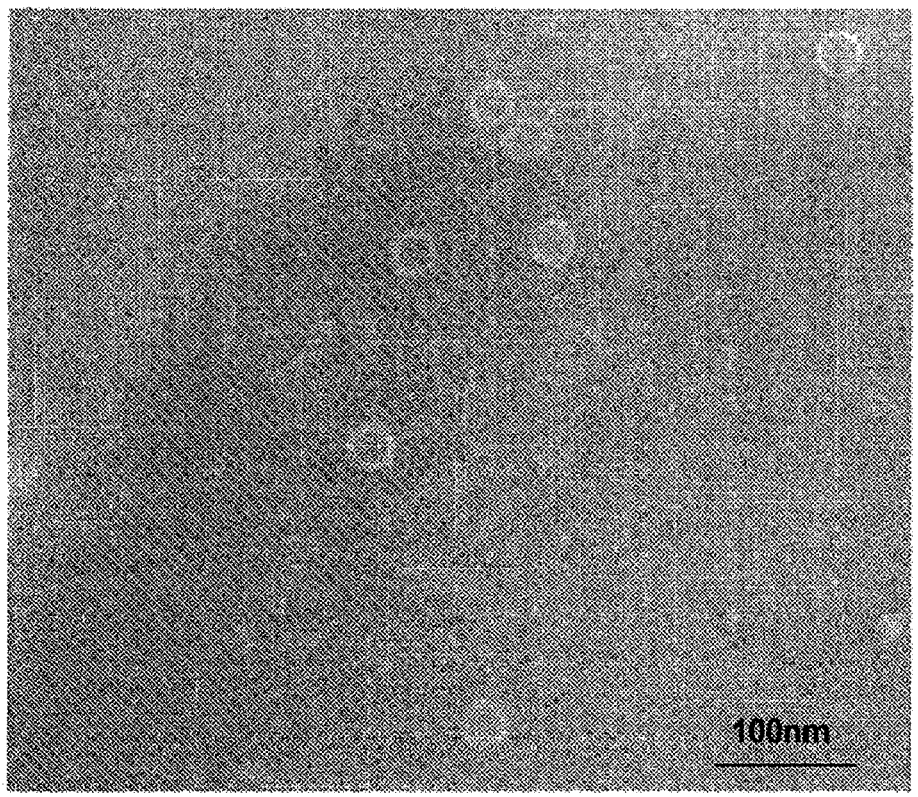
FIG. 3 is an electron micrograph of virus particles according to the present invention in Example 11.

<210> SEQ ID NO 1
<211> LENGTH: 3557
<212> TYPE: DNA
<213> ORGANISM: Magnaporthe oryzae Chrysoviirus 1

<400> SEQUENCE: 1

```
gcaaaaaara raataaagct ttcctttttt gcactcacgt ctcgcttgtt gtaractgct     60
tgttattatc ttgagctgtg tgatcgaagg aacccgactg gcttcagaca cttctgcaat    120
ggcggaaaga tacggtgagg acgtgggctc gttagggtct ggggagccgg tgttcggtgc    180
gtcgtacacc aatatctggc actctacgct actggcgagc gacgggtcgg tggccgccga    240
ggggccggcg ttgtatgcga tcgttctccc tctgagctgc ggcaaatcta gtttggcgtc    300
agtgttaagc gggtatgaca tagacgacat ggtcgtgaac gcggacgcga tgcaagcaga    360
tgacgagtgg cgcgcgatgc tcgacgcgcg gacgaagggc tgggcgtacg aagataaggc    420
agcgtaccgc ctggcgaacg acctgatgct gcgccgggca aggcggttcc ttcgttcgtt    480
tgagggtgac gacaacgccc ctgtcgtgta cgtgcacacg cgggagttgg cgacggcgct    540
ggggctgaag ataatatttg atgggtacgt ggaggaggcg gcctggctgt cctgccgccg    600
tcagctggag tcggacgcgg tgacgcgaga ccgtgacctg cgggcgtatc ggggccaagt    660
ggcagcgaac cgcgcgcacg caatacgcca tcggcaacct gagcccatcc cgttcacatc    720
gcactcccgc ttggccgaag ctgccgaagc ggcgatcagg caggctggac tgtgcgtcgg    780
gaacccgcgc gacctagcgg acagaaccag gttgtgcggc gcgcccccgc aagtcatgct    840
tgacctggcg cattcaatct gccgtgacaa gcacaggccg gcgtggttgc gggcggtggc    900
tgccaagcta ctgaggtaca ggatgggtga ggtgttgccg caggaggcgc tagcggctga    960
taactacagc gagtgggcca gggtgataca cgcggctgac caacataggg tggctgaggc   1020
gccggcgcag gagctgagag gcccgaactg gtcagaggtg ttcccgtacg gcgcaggcaa   1080
ctcgcggttt gcgttggtta agataggcga ttggattgat tatacgggca ctagcgccat   1140
gggcttcggg tatgagtggt tccggcagat ggtaaccaga cgtgaaggga cgtacgagca   1200
agcgagttgc atgctactga tgggtgatgt gtttgactac atggcccctg agttgcaccc   1260
gctgatccag cgcctgccta tggggtcgct gaagctggac cactatgcgg aggttgcaaa   1320
agagatacac cgattggtgc gctcgagtgt cacgctactg ggtcgcaggc tagacgccgg   1380
gcaactgtcc gtgtgtactt actgggactg cttggctggg cgctatttgg gttcgggcga   1440
catggagaag gagctggctg atcggactag cgagcagaag ccacgcgtct gggtatcgcg   1500
agacggaaca cagtcagccg accggttcgc gcacgagttc gcgtgcgaag tgcgcgcgct   1560
actgcaccag acgatcgctg acgggggcga gcgcatgcgt tcagtcacgg acatggtggc   1620
ctccttcgac acatttctgg agtaccgcaa gaagtgggtg aggccaggct ccgtcactgg   1680
tagccccaaa accgacattt accttcaggc cgtgagtgag cgcgagagca tgatcgcgga   1740
agttgccgac gacctggctg cgatgggtac atatgtgcta gcaaacgtcc ggctgaacaa   1800
ggccgcgact ttcgagttcc ctgagttccc cgctatagtg aagcgcgtgc tggcggacta   1860
cgtaccgaac agtttcacca gatacttcat taagaacgag atcggcaagc cggcagggcg   1920
gccgctctac ccatcacacc tcttgcacta cgtggtgggg cagttcgcgc tttacgcgct   1980
tatgaaggca cagcctatcc ctaaggtacg cttaaccgcc gaacgtgatg tggctatgga   2040
```

-continued

```
cgagcactgg atgtggatgc aggccaggga gttcactgtg ggcgtgatgc tggattacga    2100
caacttcaat gagaagcacg agtttgcgga catgcaactt attatgaggg agctgaaagg    2160
gctgtaccgc acggcgggcg tgttgagccc cgacctcaaa gccatgatag actgggtggc    2220
ggaggcgtac gaccgcactg tcttggagta cgatggggag ctgcacaact ttaagcacgg    2280
catgctgtcg gggcaggccc ccacttccgc tataaacaac ataatcaacg gcgctaataa    2340
gcggctgctg ataaggcagg tggaggagct gaccggtcgt gtgatattcc agaagcgcac    2400
gtccggcggc gacgacgtgg ccggtgagac ctattcactg tatgacgctt acctggctgt    2460
taaatgcggg cagctgatgg ggctggcctt caaggacgtg aagcagctcc tcagctccga    2520
ctactacgag ttttttccggc tgttcgtaag cgtggagggc gtgaacgggt cgctgccacg    2580
cgctttaggt agcatatgtt cgggacaatg gtcaacagc gtgaaggcta aattcgttga     2640
tccagcggca aaactgtcct cagtgaccga ggccgcattc aagatatcgc gccgcgcggg    2700
aggaaacgcc acgttccgtg agaagttgtg cgccaccgcc ttcaagaagt gggcgacgta    2760
caatgagcag gtgctggtga agggcttcat acatggcgag aggcactctg gcggtcttgg    2820
agtgcctatg agcgacggtt cggtgctcga tatagagccg atccagtggc ccgacgaaga    2880
aatggtgcga ctgaaaggac tgccctcgga cgccagtcgg gtagtggtgg ctgacgctgt    2940
tgagcaggcc gcccaactgg tcgggcgcga cagtgtcgaa gccgtcgatg ttgtcgccaa    3000
caggttgagc gagcaagtgt ttaaggcgaa tgtcgctgca atggaggggt cgagaatcgg    3060
ccaattacta gggtcatggg aagggcctcg cactgtaagg gtgcgagatg tgctgcgaat    3120
agcagaggcc gacgtggccg cgacggcgcc gaccgtggaa gagttcaggg cggcgtacgc    3180
aaaacacaag acaatgatag attattaccg gcaggtaggg gccagatacg acgcactcgc    3240
aggtgtggtc aagccgaagg cgcgtgagag gctggcgcgt gcgtcgtgca acgggacgcc    3300
gtgcgactac aagaaactgc acttctggaa ggagaagctc actatgtacg gttgcggaac    3360
gtacctgctg accgaggaca cctacgatgc tgcaagtatg ctggcgttgg tggtgagcgc    3420
ggagctatca aacagggctg taagccgcag gctggctgaa tgtgcggttg cgctgaatag    3480
ggccggaatg gtgaactact gagtgcgtgg gtgggcgccg ttccatactt cttacactgt    3540
gaggtgtaag taccca                                                    3557
```

<210> SEQ ID NO 2
<211> LENGTH: 3073
<212> TYPE: DNA
<213> ORGANISM: Magnaporthe oryzae Chrysoviirus 1

<400> SEQUENCE: 2

```
gcaaaaaaga gaataaagct ttctcctttt tgcacagtaa ctgaagcact gactggcacc      60
acatccagcc gcaacaagtc ctcagagcta ccgacaccgc cacaaacact caacaccgca    120
acacaccaac taaactagca catcatgggc ttgacgcttg acccagcaca ccggtggcgt    180
tcgaccgacc tggcgttcgc gcctgtgaat gaagtgagcg tgcaaagcgc tgtgcggggc    240
agggatgata gtgaagcggc agggacgggg ttcaccgggg ataaggccac caaggcatgg    300
tatgatggcg ccggtcgtgt gccgatcgac gacatgtgtc tggcagccgg gatgcgcgcc    360
ggcgtgctta gactggcagt ggaggtcggg tcagcgaggc ccagctcggc tgacgagtct    420
gtggtgcagt ggagatctgt gccgtactcg tacgtgggca agccgctcac agtatcgctc    480
agccacgccg ggaggcactt cgtggcgcgg ccggcgttaa cgagaatgt ggctatggcc    540 atgtacgagg caccgaccgc agacaagtgg gtggctgcga cgaacttcaa gctgccgaga    600
```

```
accgtggccg cacctggtgc cgcgccgcaa gtgccaggcc tgcccaacgg cggcggaggc    660
gctaacctgg ggttgccgaa caactttgac gcagtgcgca gggtgctcgt ggaatgcgcg    720
cgtggcgacg actacgggta taggctcttc agcatggcgc gggtggtgct gcatgctgag    780
actatgcgaa ggtcgggaat atcgccgcga gcgactccga gcatggacga ccagaacatg    840
ttcagcataa caacaggcga tacgcctcac ttaactgaag cccaaatcaa taactacgcg    900
tatgcttata atcacaccga gcaatcaccg cagtatcgag ctttcttggc gatgggggctg   960
cggggcgtgg ggcactacgc gataccccgga actatatatt ccgacggcga ctatcctgta  1020
gagtgtgccg ttaaccaccc gatcgcgttc gtccgcgtcg ggggtccccc gcctgcgaat  1080
gtggctccgg atccagctca ctacacggct gtcctgtcca acccgggcct cgctttgtca  1140
tactactggg cgtacgccta ttccatgggg ttgggccgcg tcgcggggc catactagcg    1200
caggctagca tagctccgca catctggggg tctgcggcgg tcgcacccta caagaattgc  1260
acgccaaagt tggacgcggc ggcctacttg ctgctgccag accaggagac cgcacatgtg  1320
actgcggaca gcgctcgcga gctcgtggct aacgcggccg tgctgtcgga ggcttacttg  1380
gctggaatag gggctacgct gttgagcgcg agggatagcg gcaccagga caccgcgctg   1440
atgatgcggg cggtcacaga aaagctgtcg gacccagaga cgagacgcgg tgccatgctt  1500
tctataacta gccggctgtg cccgggcggg gtggggatgg aatggctaag cccgttcagc  1560
tacgacgtct tagacggcac tgagcggtgc attagagctt ggcggaatca cggcttcttg  1620
ttggcgctat atgatacgtc gcccgtggct gctttggccc cactgttttc tacaggcgtg  1680
cctatgaata actcactgct ggataagaag agcgtggtga ccggggcgga gtaccctcag  1740
ctggtggcgt gcgcactagc gggcagggcg gagctggccg ggcggtgtga acggccgtcg  1800
cccgcctacc ttgcagcatt ggcgggccac agcgcacgca tgcgcgcgtg gaccgtagtg  1860
gtgacagtgc tgggagtggt accgccagct tcggacgacg aggaccacgc tgacgtgcaa  1920
gagcaggccg cgagcagaca agagtcgtca agcagcgtaa gaccccctcag cagccagagc 1980
gacaggagtg tcacccgggg ccacggtacc gccgagccgg cccaggcagg gcagggccg    2040
tcgagtcccc caccagtcgc gccgctgaga gggatgcggt tgggttcgcg tgcgcgcagt  2100
cataaaggct cattgtctgc accgcaagac ccgatacccg agacggggga ggagccggtc  2160
aggcaacctg acggggcagg ggcgaagcca aaggtgcagg ccatcctaga ggcgcctaaa  2220
ccggccctag agccgccctc gtggaatagc tgggcctccg aagtggcttc ggtcgaggcc  2280
aggctggcag gagcggatga agggccgagg gggaagatag tggagcccga gtaccgggggg 2340
attgcaccgt cgcgcagcac aaccacggtg gctacgtcgc ggtccgtggt gccttcagcg  2400
gcctctgcag cgtccggaac cgtggtgtca atgggcaggc gggccaaggg caaagaacga  2460
gaggtggaac gagcagacca ggttgagtca tcgagtggca gttccgacca ggccagtggg  2520
ggatcgcgcg gtgaggagct atagcgtgcc aggtaacgag acgatggttg gatgagtaac  2580
gctgctgcgg ttgggggcgtg cagccgccga tgcgtctgac ggtcgtgata acgcgtggcg  2640
ctccgggccgcg ggctgggcca cgcatccggc gaggcgcgtg ctacaaggct gtatgtttgg  2700
gtggcccgct gagctgcgcg ggcaccttaa tgagcacctc gaggacccac agctccatga  2760
tgtgacataa gataaaacaa aacaaaataa taaataaata agataagata agataaataa  2820
gataaataaa taagtaaaat gaagtaaaat aataataaaa atattaaaat aaaaatatta  2880
aaataaaata aaataacact gccgtagggt ttgcccaaca ctacgcggcc gcgtttgttg  2940
ttagaactgg gactctaaca agtgacgaac tacggatgaa gtaaatgaat caaggtagag  3000
```
tgaacactgc cgtagggttt acccaacact gcggcggtgc gcttcttgtt agaactgggg     3060
attctaacaa gta                                                         3073

<210> SEQ ID NO 3
<211> LENGTH: 3046
<212> TYPE: DNA
<213> ORGANISM: Magnaporthe oryzae Chrysoviirus 1

<400> SEQUENCE: 3
ggcaaaaaag agaataaagc tttctccttt ttgcacagca accgcggctc taccagtctc       60
ttatcttggg caacctgacg attacgctcc tcgatcgacc agattttctc aaacagcagg      120
acggtactta accactcgcg acgaccacgg cacgtgattg agatggcgat gggtacaaca      180
ggcggccagt tggcctcaaa actgcgcatc gatcaagggt tgggtttgcc agacgcgttc      240
ttacggcagg acgggaaagg tggcggggca gacggaggcg cggatggtga atgggccgcc      300
ttcgggctgc actccggagc ggcacctgac aatgcccctc cccgcgtagt gccagccgcg      360
ttggacgctt catcggggggc cgggcgaata gatacgttgc gcccgctggt ggggacgtc      420 gcttacagcc tctatttacg gctggggggag accgactatg acgtcaccaa agatgaggag      480
gccagcccaa ccgatgtgag ccactccgtg atatgctcgt acgctcttga ggtcgacggg      540
cgcacacgcg taaaccgggc cgacgtggcc tcgcactgcg ctgtttaccc cccgatggtt      600
cggcgagcga gtgcgacccc tgtgtcagtg acaggtgcgc tgacaacgtc gagactcacg      660
agtgctgccg ccgcttgcga tgggctcgcg atgcacgcag ggtcgggcaa taacgctgac      720
gtgagtctag ggataggacg cgagttcatg tacgacagag cgaggcacca ggagaatggg      780
ctcgaatccg tgttcgtccg catgtggcta gtgcacctaa gcgtgttagc gcgccaacct      840
gtgacgcaag tggtggaccc agcagtgttg tccgccaggt ttgcaaatat cgctgctccc      900
gcagagagcg acgctgctcg agccatgcgg ggggtaaaga tcaacgcccg cggacttacc      960
aacaccgcgc tggcgctgtt ggtgctaggt tgcagcgaca cctcgcaggc tgcggggctg     1020
cattatcgag cacggcgata caagtttgcg aggtccgcac tgtctatgta cggcatgcaa     1080
gggcttggca gggtggcggt tgcgctggac agggctgaag tgaccggctt agctattgta     1140
tctctagcag agaggtacgg cgcagagcat gcctgcgggg ctgggctgca gacggcattg     1200
atgatgtacg gggtgaacga tagcggaagg tatgtccaac tgaagtgtcc ggaacccgaa     1260
ttacacgacg atgtggccac cacagcagga atcagggcgc tgtcagtcaa aagttactca     1320
gacttatccg acaatcgcct gctgtcattg tccttgtttg tcggcagggc atggcgccag     1380
tcggcgggcc acctgctgcg ctcctccacc atgcagacca ccacagccga catagatgcg     1440
gtggtaaaca cactgctgcc tagccagggt gcgctgatta aggccgtggg cagtgctcac     1500
gccagagcga tgggttgggt agcgccgttg gtggacacag tgtcttatgt ggagcaaaac     1560
tatcgcctac tgtgggagga acgtggtata gtgcactgtc tcgccctcgg gctgagggtg     1620
cctaactcgg tgctggagga agccactgca gtgatagagg tcccgtaccc accggcgctg     1680
tcgccgtccg atgatcctcg ttctgccggg ccgcgggctg gcagcctagc caccctcgga     1740
ttagtggagt cgctgctgtc gtcatcgggc gagggactat gcgggtcagc gcgggctcga     1800
gggagacgcc aagctgggct tgtagcggtg ccggcacagg tggttgcatt ggctggacac     1860
cgggtgcagt tcaccctgct gagcgtagct agcggggtag ctgtgagagt ggaagagctg     1920
ccaacccggc cgctactggc tgagccgctg caaaccgggc tggaggcagt cgagtacgtg     1980
caagtgccgt gggcccccagc ccaggcagct cctgcgcccg cgcctcctgt ggagtttcgc     2040

```
gacactctgg atcagttcct gcacgcctac aagccgagta ggtcagtgtt ggagcagcct    2100
agggtggagg taacgcccag gatgcagtcg ggatcggacg tccttaacgt cgtgttgcct    2160
gaagatacgc ctgccccctt gcgcgactct atcatgggcg gcacattgac ccccgtcagc    2220
gccgcaggtg tgggcggctg tgcggaggcg atagtgaact cattgcaggc acagtatggg    2280
gtgacagtct cgaccggcga gatagaaaag gagctgcagg gggaccactc gggtggcgag    2340
ctgctgcagg tgggggcgat ggcctcggcg ctggccaagt ttggggacta ccggctagtc    2400
ttgctcgacg aacactcgca gggggtaatt ctgagggcgg gcgatagcgg gagcaagccc    2460
gtcacaatac acaggaatgg tgcgtcttac aacgcactgg ggcgtgggcc gggccgcgca    2520 atacggggttg ggctgcgcag ccacgggcca ccggcacgcg agccgcagcg tgagccgcgt    2580
cgcatgtcac gcagcagctg agttgcgtga ggccgcaggc gggcaccgct gcccagggtg    2640
gctggggcga gagctgtaat cgcaggtttc acggcacgct tcggcaccac attgaggcga    2700
ccagctcctc gagatgcggg cgtcgcgccg gcgcgtgacc gcgcgcgcac cgcttggcgt    2760
ggatgggtgc gcaccgccct gtacaaccga gcagccgacc ataggggccg ctaacggagc    2820
gtccggcgcc tgccgaggcg gcgcacctcc tgtcgggcgt ggtgtccggg caagcaacac    2880
catggagtag tcagccagaa caaaacaaaa caaaaacaaa aacaaaaaca aacacaaaaa    2940
caaaaccaaa accacaagaa aaactaaaat caaccactgc cgctgggttt acacagcctc    3000
gcggcagtgc gcttcttgtt aaacctaggg ttctaacaag tacsmt                   3046

<210> SEQ ID NO 4
<211> LENGTH: 2383
<212> TYPE: DNA
<213> ORGANISM: Magnaporthe oryzae Chrysoviirus 1

<400> SEQUENCE: 4
tcgaacgcag cgaccaccac caccacgcgg agctgggttc gacacagcga tgggtcagtc      60
agtgtacgaa ccgagcgcag aattaccaac agagacccag caatcgtacg cgctatcgcc     120
cggttcattt cagggtgatg ctctcgctgc gctttcgaca ctgggcaagg tgccggcgct     180
ggaggtcgcg gggatagtta ggcgcggggc gaccgttcta gggaagcttg ctccgccgag     240
tgaggatcag acgtacgccc gcttgtacag ggaggctcgc gattacgtgg gcaataacac     300
ggaagcggag gttgaacgcc cagtcgacag agtgtgggcc gagacctcag agcctcgctt     360
gtctcgtact gccatggcgc gcgccgaccc ggacacgcag tggcagccgg ggctgtacct     420
cgggatgccg tacggcccgg acgctgctag aattgtcgcc caaccgttgg acgcgcggga     480
gccaggccac ttcagcaacc tagccccctg gatcgtcggc gtgttgaacg gcaccacagg     540
cgcgttcgag ggcgatgcgc tgaggctctc agccaggaca accccgcatg tggatgacgg     600
ctggttgggt gcacaggctc tgactaggca cgacatcgac gtgaggttgg cgccgtcgaa     660
cgcggcctgt actgtctcgg tactggttgg cgtcgactac gtggccggga agccggtgct     720
acaccacatg gcggtggcgg gctatcagga cgccagaccg cctctaaggc gcctcaccct     780
ggcgctgtgc gaggcgctca catacccatgt cgcagtgggt ggagtactcc cggtgaacgc     840
agtgcacaag cgccaatgct caaactacac cgacataatg tctgcggagg catacagcga     900
cccgcccgcg cccaaccaac tgggcccacg cgtgtccacg aacccgccgg aggggtgttt     960
ggcacaactg gtgcaagtac accaatatga cgtgcaaacc ggggtgtcga caggagtgat    1020
gtcggcgcga gacgtgcccc cgtccgcctt ctacttcggg gggacaccta acggccgaaa    1080
cacagggtac gccataatgc gtgtggaagt ggacggcgtg atcactcacg tgttgacagg    1140
```

-continued

```
ggctgttcat atgaaagggc accccgcgtt tctgttgtca gggcgtaggc gtcagccatg   1200
cgtgagggac ggcttgtact cacctggcgc tgtctgtaag ctgttcggcg atgggggcgg   1260
cggtttgtgc atgcgcgcgg aggatgcctc gggggcagat cgcgagctac gcacggtgtg   1320
gtctgacgcg ctgtcgaacg aaaacaaaac cgcggcggta cgttcgcgag acccgctgtc   1380
agcagcgagc ctcctgatag ccatagctaa gctgaacggg tggcaagcta ggccggccgg   1440
cccgcacagc attactgcag acaccgacag gggcgaagtg cgggtgttcg tggagttttg   1500
gcccacgtca ggtccacggt ggcttgaggt ggtgtcgttt gacgaggagg tggacctcgg   1560
accggaaggc gacgacgggc aatgcgacca tccgtctgag ctggcgctgg actactggct   1620
gtcaggcttg gcgaggtaca tgctcaagga tataacccgg aacggatacc tcattaaagg   1680
ctgcgggaag tacgctcgca atgagtcgtc ccctttccaa gcgcaacaca cagccgctcc   1740
gcaagcttca tgcgatgtgg tggtgagtgc gtggcgggta gaaaccaaga ttggcccagc   1800
gaaggcgtcc tacatgtaca acttaggtgt ggctgtgtgc gccgccggag ccgtagttgc   1860
cacatctaac ctagttgatg tgaacgcgga aatccgacgt ggcgcagtag tcggcaatgg   1920
gaatgtgcta gctgcgtacg ataggcgcac ccgatcagaa gtcgcacgcg ctgacctgct   1980
tgctgtgctg aaaggactgt cgagactggc gatggcgggg tccgtgcgtg tgtacagcgc   2040
cacccaagct ggcaacgacc aggcggacgt gaatgtgctg aggagcgacg gtaagagcgg   2100
gccaagtgcg agaataatgg agatagggac gctggtggag agacgaggca gcgcggctga   2160
tgccggagcg gacgcttcag gagcagcggt gtcaagcggc gtggctgcgg atacaggaca   2220
acccgtgact ttagcgggag ccgatgagtt atgggcaact ctgcggcgtt tggtgcggtg   2280
agtgctcgga caggtggcgc tgaggcgacg cctagtagct gcttgcagtg tctgcgtggc   2340
caccgttacg aattcaaact tcttacgtgt caacgtaagt acc                     2383

<210> SEQ ID NO 5
<211> LENGTH: 1127
<212> TYPE: PRT
<213> ORGANISM: Magnaporthe oryzae Chrysoviirus 1

<400> SEQUENCE: 5

Met Ala Glu Arg Tyr Gly Glu Asp Val Gly Ser Leu Gly Ser Gly Glu
1               5                   10                  15

Pro Val Phe Gly Ala Ser Tyr Thr Asn Ile Trp His Ser Thr Leu Leu
            20                  25                  30

Ala Ser Asp Gly Ser Val Ala Ala Glu Gly Pro Ala Leu Tyr Ala Ile
        35                  40                  45

Val Leu Pro Leu Ser Cys Gly Lys Ser Ser Leu Ala Ser Val Leu Ser
    50                  55                  60

Gly Tyr Asp Ile Asp Asp Met Val Val Asn Ala Asp Ala Met Gln Ala
65                  70                  75                  80

Asp Asp Glu Trp Arg Ala Met Leu Asp Ala Arg Thr Lys Gly Trp Ala
                85                  90                  95

Tyr Glu Asp Lys Ala Ala Tyr Arg Leu Ala Asn Asp Leu Met Leu Arg
            100                 105                 110

Arg Ala Arg Arg Phe Leu Arg Ser Phe Glu Gly Asp Asp Asn Ala Pro
        115                 120                 125

Val Val Tyr Val His Thr Arg Glu Leu Ala Thr Ala Leu Gly Leu Lys
    130                 135                 140

Ile Ile Phe Asp Gly Tyr Val Glu Glu Ala Ala Trp Leu Ser Cys Arg
145                 150                 155                 160
```

```
Arg Gln Leu Glu Ser Asp Ala Val Thr Arg Asp Arg Asp Leu Arg Ala
                165                 170                 175

Tyr Arg Gly Gln Val Ala Ala Asn Arg Ala His Ala Ile Arg His Arg
            180                 185                 190

Gln Pro Glu Pro Ile Pro Phe Thr Ser His Ser Arg Leu Ala Glu Ala
        195                 200                 205

Ala Glu Ala Ala Ile Arg Gln Ala Gly Leu Cys Val Gly Asn Pro Arg
    210                 215                 220

Asp Leu Ala Asp Arg Thr Arg Leu Cys Gly Ala Pro Pro Gln Val Met
225                 230                 235                 240

Leu Asp Leu Ala His Ser Ile Cys Arg Asp Lys His Arg Pro Ala Trp
                245                 250                 255

Leu Arg Ala Val Ala Ala Lys Leu Leu Arg Tyr Arg Met Gly Glu Val
            260                 265                 270

Leu Pro Gln Glu Ala Leu Ala Ala Asp Asn Tyr Ser Glu Trp Ala Arg
        275                 280                 285

Val Ile His Ala Ala Asp Gln His Arg Val Ala Glu Ala Pro Ala Gln
    290                 295                 300

Glu Leu Arg Gly Pro Asn Trp Ser Glu Val Phe Pro Tyr Gly Ala Gly
305                 310                 315                 320

Asn Ser Arg Phe Ala Leu Val Lys Ile Gly Asp Trp Ile Asp Tyr Thr
                325                 330                 335

Gly Thr Ser Ala Met Gly Phe Gly Tyr Glu Trp Phe Arg Gln Met Val
            340                 345                 350

Thr Arg Arg Glu Gly Thr Tyr Glu Gln Ala Ser Cys Met Leu Leu Met
        355                 360                 365

Gly Asp Val Phe Asp Tyr Met Ala Pro Glu Leu His Pro Leu Ile Gln
    370                 375                 380

Arg Leu Pro Met Gly Ser Leu Lys Leu Asp His Tyr Ala Glu Val Ala
385                 390                 395                 400

Lys Glu Ile His Arg Leu Val Arg Ser Ser Val Thr Leu Leu Gly Arg
                405                 410                 415

Arg Leu Asp Ala Gly Gln Leu Ser Val Cys Thr Tyr Trp Asp Cys Leu
            420                 425                 430

Ala Gly Arg Tyr Leu Gly Ser Gly Asp Met Glu Lys Glu Leu Ala Asp
        435                 440                 445

Arg Thr Ser Glu Gln Lys Pro Arg Val Trp Val Ser Arg Asp Gly Thr
    450                 455                 460

Gln Ser Ala Asp Arg Phe Ala His Glu Phe Ala Cys Glu Val Arg Ala
465                 470                 475                 480

Leu Leu His Gln Thr Ile Ala Asp Gly Gly Glu Arg Met Arg Ser Val
                485                 490                 495

Thr Asp Met Val Ala Ser Phe Asp Thr Phe Leu Glu Tyr Arg Lys Lys
            500                 505                 510

Trp Val Arg Pro Gly Ser Val Thr Gly Ser Pro Lys Thr Asp Ile Tyr
        515                 520                 525

Leu Gln Ala Val Ser Glu Arg Glu Ser Met Ile Ala Glu Val Ala Asp
    530                 535                 540

Asp Leu Ala Ala Met Gly Thr Tyr Val Leu Ala Asn Val Arg Leu Asn
545                 550                 555                 560

Lys Ala Ala Thr Phe Glu Phe Pro Glu Phe Pro Ala Ile Val Lys Arg
                565                 570                 575

Val Leu Ala Asp Tyr Val Pro Asn Ser Phe Thr Arg Tyr Phe Ile Lys
            580                 585                 590
```

```
Asn Glu Ile Gly Lys Pro Ala Gly Arg Pro Leu Tyr Pro Ser His Leu
            595                 600                 605

Leu His Tyr Val Val Gly Gln Phe Ala Leu Tyr Ala Leu Met Lys Ala
            610                 615                 620

Gln Pro Ile Pro Lys Val Arg Leu Thr Ala Glu Arg Asp Val Ala Met
625                 630                 635                 640

Asp Glu His Trp Met Trp Met Gln Ala Arg Glu Phe Thr Val Gly Val
                645                 650                 655

Met Leu Asp Tyr Asp Asn Phe Asn Glu Lys His Glu Phe Ala Asp Met
            660                 665                 670

Gln Leu Ile Met Arg Glu Leu Lys Gly Leu Tyr Arg Thr Ala Gly Val
            675                 680                 685

Leu Ser Pro Asp Leu Lys Ala Met Ile Asp Trp Val Ala Glu Ala Tyr
            690                 695                 700

Asp Arg Thr Val Leu Glu Tyr Asp Gly Glu Leu His Asn Phe Lys His
705                 710                 715                 720

Gly Met Leu Ser Gly Gln Ala Pro Thr Ser Ala Ile Asn Asn Ile Ile
                725                 730                 735

Asn Gly Ala Asn Lys Arg Leu Leu Ile Arg Gln Val Glu Glu Leu Thr
            740                 745                 750

Gly Arg Val Ile Phe Gln Lys Arg Thr Ser Gly Gly Asp Asp Val Ala
            755                 760                 765

Gly Glu Thr Tyr Ser Leu Tyr Asp Ala Tyr Leu Ala Val Lys Cys Gly
            770                 775                 780

Gln Leu Met Gly Leu Ala Phe Lys Asp Val Lys Gln Leu Leu Ser Ser
785                 790                 795                 800

Asp Tyr Tyr Glu Phe Phe Arg Leu Phe Val Ser Val Glu Gly Val Asn
                805                 810                 815

Gly Ser Leu Pro Arg Ala Leu Gly Ser Ile Cys Ser Gly Gln Trp Ser
            820                 825                 830

Asn Ser Val Lys Ala Lys Phe Val Asp Pro Ala Ala Lys Leu Ser Ser
            835                 840                 845

Val Thr Glu Ala Ala Phe Lys Ile Ser Arg Arg Ala Gly Gly Asn Ala
            850                 855                 860

Thr Phe Arg Glu Lys Leu Cys Ala Thr Ala Phe Lys Lys Trp Ala Thr
865                 870                 875                 880

Tyr Asn Glu Gln Val Leu Val Lys Gly Phe Ile His Gly Glu Arg His
                885                 890                 895

Ser Gly Gly Leu Gly Val Pro Met Ser Asp Gly Ser Val Leu Asp Ile
            900                 905                 910

Glu Pro Ile Gln Trp Pro Asp Glu Met Val Arg Leu Lys Gly Leu
            915                 920                 925

Pro Ser Asp Ala Ser Arg Val Val Ala Asp Ala Val Glu Gln Ala
930                 935                 940

Ala Gln Leu Val Gly Arg Asp Ser Val Glu Ala Val Asp Val Ala
945                 950                 955                 960

Asn Arg Leu Ser Glu Gln Val Phe Lys Ala Asn Val Ala Ala Met Glu
            965                 970                 975

Gly Ser Arg Ile Gly Gln Leu Leu Gly Ser Trp Glu Gly Pro Arg Thr
            980                 985                 990

Val Arg Val Arg Asp Val Leu Arg  Ile Ala Glu Ala Asp  Val Ala Ala
            995                 1000                1005

Thr Ala  Pro Thr Val Glu Glu  Phe Arg Ala Ala Tyr  Ala Lys His
```

```
    1010                1015                1020

Lys Thr  Met Ile Asp Tyr Tyr  Arg Gln Val Gly Ala  Arg Tyr Asp
    1025                1030                1035

Ala Leu  Ala Gly Val Val Lys  Pro Lys Ala Arg Glu  Arg Leu Ala
    1040                1045                1050

Arg Ala  Ser Cys Asn Gly Thr  Pro Cys Asp Tyr Lys  Lys Leu His
    1055                1060                1065

Phe Trp  Lys Glu Lys Leu Thr  Met Tyr Gly Cys Gly  Thr Tyr Leu
    1070                1075                1080

Leu Thr  Glu Asp Thr Tyr Asp  Ala Ala Ser Met Leu  Ala Leu Val
    1085                1090                1095

Val Ser  Ala Glu Leu Ser Asn  Glu Ala Val Ser Arg  Arg Leu Ala
    1100                1105                1110

Glu Cys  Ala Val Ala Leu Asn  Arg Ala Gly Met Val  Asn Tyr
    1115                1120                1125

<210> SEQ ID NO 6
<211> LENGTH: 801
<212> TYPE: PRT
<213> ORGANISM: Magnaporthe oryzae Chrysoviirus 1

<400> SEQUENCE: 6

Met Gly Leu Thr Leu Asp Pro Ala His Arg Trp Arg Ser Thr Asp Leu
1               5                   10                  15

Ala Phe Ala Pro Val Asn Glu Val Ser Val Gln Ser Ala Val Arg Gly
            20                  25                  30

Arg Asp Asp Ser Glu Ala Ala Gly Thr Gly Phe Thr Gly Asp Lys Ala
        35                  40                  45

Thr Lys Ala Trp Tyr Asp Gly Ala Gly Arg Val Pro Ile Asp Asp Met
    50                  55                  60

Cys Leu Ala Ala Gly Met Arg Ala Gly Val Leu Arg Leu Ala Val Glu
65                  70                  75                  80

Val Gly Ser Ala Arg Pro Ser Ser Ala Asp Glu Ser Val Val Gln Trp
                85                  90                  95

Arg Ser Val Pro Tyr Ser Tyr Val Gly Lys Pro Leu Thr Val Ser Leu
            100                 105                 110

Ser His Ala Gly Arg His Phe Val Ala Arg Pro Ala Leu Asn Glu Asn
        115                 120                 125

Val Ala Met Ala Ala Cys Met Tyr Glu Ala Pro Thr Ala Asp Lys Trp
    130                 135                 140

Val Ala Ala Thr Asn Phe Lys Leu Pro Arg Thr Val Ala Ala Pro Gly
145                 150                 155                 160

Ala Ala Pro Gln Val Pro Gly Leu Pro Asn Gly Gly Gly Gly Ala Asn
                165                 170                 175

Leu Gly Leu Pro Asn Asn Phe Asp Ala Val Arg Arg Val Leu Val Glu
            180                 185                 190

Cys Ala Arg Gly Asp Asp Tyr Gly Tyr Arg Leu Phe Ser Met Ala Arg
        195                 200                 205

Val Val Leu His Ala Glu Thr Met Arg Arg Ser Gly Ile Ser Pro Arg
    210                 215                 220

Ala Thr Pro Ser Met Asp Asp Gln Asn Met Phe Ser Ile Thr Thr Gly
225                 230                 235                 240

Asp Thr Pro His Leu Thr Glu Ala Gln Ile Asn Asn Tyr Ala Tyr Ala
                245                 250                 255

Tyr Asn His Thr Glu Gln Ser Pro Gln Tyr Arg Ala Phe Leu Ala Met
```

```
                260                 265                 270
Gly Leu Arg Gly Val Gly His Tyr Ala Ile Pro Gly Thr Ile Tyr Ser
            275                 280                 285
Asp Gly Asp Tyr Pro Val Glu Cys Ala Val Asn His Pro Ile Ala Phe
        290                 295                 300
Val Arg Val Gly Gly Pro Pro Ala Asn Val Ala Pro Asp Pro Ala
305                 310                 315                 320
His Tyr Thr Ala Val Leu Ser Asn Pro Gly Leu Ala Leu Ser Tyr Tyr
                325                 330                 335
Trp Ala Tyr Ala Tyr Ser Met Gly Leu Gly Arg Val Ala Gly Ala Ile
            340                 345                 350
Leu Ala Gln Ala Ser Ile Ala Pro His Ile Trp Gly Ser Ala Ala Val
                355                 360                 365
Ala Pro Tyr Lys Asn Cys Thr Pro Lys Leu Asp Ala Ala Tyr Leu
        370                 375                 380
Leu Leu Pro Asp Gln Glu Thr Ala His Val Thr Ala Asp Ser Ala Arg
385                 390                 395                 400
Glu Leu Val Ala Asn Ala Ala Val Leu Ser Glu Ala Tyr Leu Ala Gly
                405                 410                 415
Ile Gly Ala Thr Leu Leu Ser Ala Arg Asp Ser Gly His Gln Asp Thr
            420                 425                 430
Ala Leu Met Met Arg Ala Val Thr Glu Lys Leu Ser Asp Pro Glu Thr
                435                 440                 445
Arg Arg Gly Ala Met Leu Ser Ile Thr Ser Arg Leu Cys Pro Gly Gly
        450                 455                 460
Val Gly Met Glu Trp Leu Ser Pro Phe Ser Tyr Asp Val Leu Asp Gly
465                 470                 475                 480
Thr Glu Arg Cys Ile Arg Ala Trp Arg Asn His Gly Phe Leu Leu Ala
                485                 490                 495
Leu Tyr Asp Thr Ser Pro Val Ala Ala Leu Ala Pro Leu Phe Ser Thr
            500                 505                 510
Gly Val Pro Met Asn Asn Ser Leu Leu Asp Lys Lys Ser Val Val Thr
        515                 520                 525
Gly Ala Glu Tyr Pro Gln Leu Val Ala Cys Ala Leu Ala Gly Arg Ala
        530                 535                 540
Glu Leu Ala Gly Arg Cys Glu Arg Pro Ser Pro Ala Tyr Leu Ala Ala
545                 550                 555                 560
Leu Ala Gly His Ser Ala Arg Met Arg Ala Trp Thr Val Val Thr
            565                 570                 575
Val Leu Gly Val Val Pro Pro Ala Ser Asp Asp Glu Asp His Ala Asp
        580                 585                 590
Val Gln Glu Gln Ala Ala Ser Arg Gln Glu Ser Ser Ser Val Arg
            595                 600                 605
Pro Leu Ser Ser Gln Ser Asp Arg Ser Val Thr Arg Gly His Gly Thr
        610                 615                 620
Ala Glu Pro Ala Gln Ala Gly Ala Gly Pro Ser Ser Pro Pro Val
625                 630                 635                 640
Ala Pro Leu Arg Gly Met Arg Leu Gly Ser Arg Ala Arg Ser His Lys
            645                 650                 655
Gly Ser Leu Ser Ala Pro Gln Asp Pro Ile Pro Glu Thr Gly Glu Glu
            660                 665                 670
Pro Val Arg Gln Pro Asp Gly Ala Gly Ala Lys Pro Lys Val Gln Ala
        675                 680                 685
```

Ile Leu Glu Ala Pro Lys Pro Ala Leu Glu Pro Pro Ser Trp Asn Ser
690 695 700

Trp Ala Ser Glu Val Ala Ser Val Glu Ala Arg Leu Ala Gly Ala Asp
705 710 715 720

Glu Gly Pro Arg Gly Lys Ile Val Glu Pro Glu Tyr Arg Gly Ile Ala
725 730 735

Pro Ser Arg Ser Thr Thr Thr Val Ala Thr Ser Arg Ser Val Val Pro
740 745 750

Ser Ala Ala Ser Ala Ala Ser Gly Thr Val Val Ser Met Gly Arg Arg
755 760 765

Ala Lys Gly Lys Glu Arg Glu Val Glu Arg Ala Asp Gln Val Glu Ser
770 775 780

Ser Ser Gly Ser Ser Asp Gln Ala Ser Gly Gly Ser Arg Gly Glu Glu
785 790 795 800

Leu

<210> SEQ ID NO 7
<211> LENGTH: 812
<212> TYPE: PRT
<213> ORGANISM: Magnaporthe oryzae Chrysoviirus 1

<400> SEQUENCE: 7

Met Ala Met Gly Thr Thr Gly Gly Gln Leu Ala Ser Lys Leu Arg Ile
1 5 10 15

Asp Gln Gly Leu Gly Leu Pro Asp Ala Phe Leu Arg Gln Asp Gly Lys
20 25 30

Gly Gly Gly Ala Asp Gly Gly Ala Asp Gly Glu Trp Ala Ala Phe Gly
35 40 45

Leu His Ser Gly Ala Ala Pro Asp Asn Ala Pro Pro Arg Val Val Pro
50 55 60

Ala Ala Leu Asp Ala Ser Ser Gly Ala Gly Arg Ile Asp Thr Leu Arg
65 70 75 80

Pro Leu Val Gly Asp Val Ala Tyr Ser Leu Tyr Leu Arg Leu Gly Glu
85 90 95

Thr Asp Tyr Asp Val Thr Lys Asp Glu Glu Ala Ser Pro Thr Asp Val
100 105 110

Ser His Ser Val Ile Cys Ser Tyr Ala Leu Glu Val Asp Gly Arg Thr
115 120 125

Ala Leu Asn Arg Ala Asp Val Ala Ser His Cys Ala Val Tyr Pro Pro
130 135 140

Met Val Arg Arg Ala Ser Ala Thr Pro Val Ser Val Thr Gly Ala Leu
145 150 155 160

Thr Thr Ser Arg Leu Thr Ser Ala Ala Ala Ala Cys Asp Gly Leu Ala
165 170 175

Met His Ala Gly Ser Gly Asn Asn Ala Asp Val Ser Leu Gly Ile Gly
180 185 190

Arg Glu Phe Met Tyr Asp Arg Ala Arg His Gln Glu Asn Gly Leu Glu
195 200 205

Ser Val Phe Val Arg Met Trp Leu Val His Leu Ser Val Leu Ala Arg
210 215 220

Gln Pro Val Thr Gln Val Val Asp Pro Ala Val Leu Ser Ala Arg Phe
225 230 235 240

Ala Asn Ile Ala Ala Pro Ala Glu Ser Asp Ala Ala Arg Ala Met Arg
245 250 255

Gly Val Lys Ile Asn Ala Arg Gly Leu Thr Asn Thr Ala Leu Ala Leu

```
                    260             265                 270
Leu Val Leu Gly Cys Ser Asp Thr Ser Gln Ala Ala Gly Leu His Tyr
            275                 280             285

Arg Ala Arg Arg Tyr Lys Phe Ala Arg Ser Ala Leu Ser Met Tyr Gly
        290                 295             300

Met Gln Gly Leu Gly Arg Val Ala Val Ala Leu Asp Arg Ala Glu Val
305                 310             315                 320

Thr Gly Leu Ala Ile Val Ser Leu Ala Glu Arg Tyr Gly Ala Glu His
                325             330             335

Ala Cys Gly Ala Gly Leu Gln Thr Ala Leu Met Met Tyr Gly Val Asn
            340             345             350

Asp Ser Gly Arg Tyr Val Gln Leu Lys Cys Pro Glu Pro Glu Leu His
        355             360             365

Asp Asp Val Ala Thr Thr Ala Gly Ile Arg Ala Leu Ser Val Lys Ser
        370             375             380

Tyr Ser Asp Leu Ser Asp Asn Arg Leu Leu Ser Leu Ser Leu Phe Val
385             390             395             400

Gly Arg Ala Trp Arg Gln Ser Ala Gly His Leu Leu Arg Ser Ser Thr
                405             410             415

Met Gln Thr Thr Thr Ala Asp Ile Asp Ala Val Val Asn Thr Leu Leu
            420             425             430

Pro Ser Gln Gly Ala Leu Ile Lys Ala Val Gly Ser Ala His Ala Arg
            435             440             445

Ala Met Gly Trp Val Ala Pro Leu Val Asp Thr Val Ser Tyr Val Glu
        450             455             460

Gln Asn Tyr Arg Leu Leu Trp Glu Glu Arg Gly Ile Val His Cys Leu
465             470             475             480

Ala Leu Gly Leu Arg Val Pro Asn Ser Val Leu Glu Glu Ala Thr Ala
                485             490             495

Val Ile Glu Val Pro Tyr Pro Pro Ala Leu Ser Pro Ser Asp Asp Pro
            500             505             510

Arg Ser Ala Gly Pro Arg Ala Gly Ser Leu Ala Thr Leu Gly Leu Val
        515             520             525

Glu Ser Leu Leu Ser Ser Ser Gly Glu Gly Leu Cys Gly Ser Ala Arg
    530             535             540

Ala Arg Gly Arg Arg Gln Ala Gly Leu Val Ala Val Pro Ala Gln Val
545             550             555             560

Val Ala Leu Ala Gly His Arg Val Gln Phe Thr Leu Leu Ser Val Ala
                565             570             575

Ser Gly Val Ala Val Arg Val Glu Glu Leu Pro Thr Arg Pro Leu Leu
            580             585             590

Ala Glu Pro Leu Gln Thr Gly Leu Glu Ala Val Glu Tyr Val Gln Val
        595             600             605

Pro Trp Ala Pro Ala Gln Ala Pro Ala Pro Pro Val Glu
    610             615             620

Phe Arg Asp Thr Leu Asp Gln Phe Leu His Ala Tyr Lys Pro Ser Arg
625             630             635             640

Ser Val Leu Glu Gln Pro Arg Val Glu Val Thr Pro Arg Met Gln Ser
                645             650             655

Gly Ser Asp Val Leu Asn Val Leu Pro Glu Asp Thr Pro Ala Pro
            660             665             670

Leu Arg Asp Ser Ile Met Gly Gly Thr Leu Thr Pro Val Ser Ala Ala
            675             680             685
```

Gly Val Gly Gly Cys Ala Glu Ala Ile Val Asn Ser Leu Gln Ala Gln
        690                 695                 700

Tyr Gly Val Thr Val Ser Thr Gly Glu Ile Glu Lys Glu Leu Gln Gly
705                 710                 715                 720

Asp His Ser Gly Gly Glu Leu Leu Gln Val Gly Ala Met Ala Ser Ala
                725                 730                 735

Leu Ala Lys Phe Gly Asp Tyr Arg Leu Val Leu Asp Glu His Ser
            740                 745                 750

Gln Gly Val Ile Leu Arg Ala Gly Asp Ser Gly Ser Lys Pro Val Thr
            755                 760                 765

Ile His Arg Asn Gly Ala Ser Tyr Asn Ala Leu Gly Arg Gly Pro Gly
        770                 775                 780

Arg Ala Ile Arg Val Gly Leu Arg Ser His Gly Pro Pro Ala Arg Glu
785                 790                 795                 800

Pro Gln Arg Glu Pro Arg Arg Met Ser Arg Ser Ser
                805                 810

<210> SEQ ID NO 8
<211> LENGTH: 743
<212> TYPE: PRT
<213> ORGANISM: Magnaporthe oryzae Chrysoviirus 1

<400> SEQUENCE: 8

Met Gly Gln Ser Val Tyr Glu Pro Ser Ala Glu Leu Pro Thr Glu Thr
1               5                   10                  15

Gln Gln Ser Tyr Ala Leu Ser Pro Gly Ser Phe Gln Gly Asp Ala Leu
            20                  25                  30

Ala Ala Leu Ser Thr Leu Gly Lys Val Pro Ala Leu Glu Val Ala Gly
        35                  40                  45

Ile Val Arg Arg Gly Ala Thr Val Leu Gly Lys Leu Ala Pro Pro Ser
    50                  55                  60

Glu Asp Gln Thr Tyr Ala Arg Leu Tyr Arg Glu Ala Arg Asp Tyr Val
65                  70                  75                  80

Gly Asn Asn Thr Glu Ala Glu Val Glu Arg Pro Val Asp Arg Val Trp
                85                  90                  95

Ala Glu Thr Ser Glu Pro Arg Leu Ser Arg Thr Ala Met Ala Arg Ala
            100                 105                 110

Asp Pro Asp Thr Gln Trp Gln Pro Gly Leu Tyr Leu Gly Met Pro Tyr
        115                 120                 125

Gly Pro Asp Ala Ala Arg Ile Val Ala Gln Pro Leu Asp Ala Arg Glu
    130                 135                 140

Pro Gly His Phe Ser Asn Leu Ala Pro Trp Ile Val Gly Val Leu Asn
145                 150                 155                 160

Gly Thr Thr Gly Ala Phe Glu Gly Asp Ala Leu Arg Leu Ser Ala Arg
                165                 170                 175

Thr Thr Pro His Val Asp Asp Gly Trp Leu Gly Ala Gln Ala Leu Thr
            180                 185                 190

Arg His Asp Ile Asp Val Arg Leu Ala Pro Ser Asn Ala Ala Cys Thr
        195                 200                 205

Val Ser Val Leu Val Gly Val Asp Tyr Val Ala Gly Lys Pro Val Leu
    210                 215                 220

His His Met Ala Val Ala Gly Tyr Gln Asp Ala Arg Pro Pro Leu Arg
225                 230                 235                 240

Arg Leu Thr Leu Ala Leu Cys Glu Ala Leu Thr Tyr His Val Ala Val
                245                 250                 255

```
Gly Gly Val Leu Pro Val Asn Ala Val His Lys Arg Gln Cys Ser Asn
            260                 265                 270

Tyr Thr Asp Ile Met Ser Ala Glu Ala Tyr Ser Asp Pro Ala Pro
        275                 280                 285

Asn Gln Leu Gly Pro Arg Val Ser Thr Asn Pro Pro Glu Gly Cys Leu
    290                 295                 300

Ala Gln Leu Val Gln Val His Gln Tyr Asp Val Gln Thr Gly Val Ser
305                 310                 315                 320

Thr Gly Val Met Ser Ala Arg Asp Val Pro Pro Ser Ala Phe Tyr Phe
                325                 330                 335

Gly Gly Thr Pro Asn Gly Arg Asn Thr Gly Tyr Ala Ile Met Arg Val
            340                 345                 350

Glu Val Asp Gly Val Ile Thr His Val Leu Thr Gly Ala Val His Met
        355                 360                 365

Lys Gly His Pro Ala Phe Leu Leu Ser Gly Arg Arg Gln Pro Cys
    370                 375                 380

Val Arg Asp Gly Leu Tyr Ser Pro Gly Ala Val Cys Lys Leu Phe Gly
385                 390                 395                 400

Asp Gly Gly Gly Leu Cys Met Arg Ala Glu Asp Ala Ser Gly Ala
                405                 410                 415

Asp Arg Glu Leu Arg Thr Val Trp Ser Asp Ala Leu Ser Asn Glu Asn
                420                 425                 430

Lys Thr Ala Ala Val Arg Ser Arg Asp Pro Leu Ser Ala Ala Ser Leu
            435                 440                 445

Leu Ile Ala Ile Ala Lys Leu Asn Gly Trp Gln Ala Arg Pro Ala Gly
        450                 455                 460

Pro His Ser Ile Thr Ala Asp Thr Asp Arg Gly Glu Val Arg Val Phe
465                 470                 475                 480

Val Glu Phe Trp Pro Thr Ser Gly Pro Arg Trp Leu Glu Val Val Ser
                485                 490                 495

Phe Asp Glu Glu Val Asp Leu Gly Pro Glu Gly Asp Asp Gly Gln Cys
                500                 505                 510

Asp His Pro Ser Glu Leu Ala Leu Asp Tyr Trp Leu Ser Gly Leu Ala
            515                 520                 525

Arg Tyr Met Leu Lys Asp Ile Thr Arg Asn Gly Tyr Leu Ile Lys Gly
        530                 535                 540

Cys Gly Lys Tyr Ala Arg Asn Glu Ser Ser Pro Phe Gln Ala Gln His
545                 550                 555                 560

Thr Ala Ala Pro Gln Ala Ser Cys Asp Val Val Ser Ala Trp Arg
                565                 570                 575

Val Glu Thr Lys Ile Gly Pro Ala Lys Ala Ser Tyr Met Tyr Asn Leu
            580                 585                 590

Gly Val Ala Val Cys Ala Ala Gly Ala Val Ala Thr Ser Asn Leu
        595                 600                 605

Val Asp Val Asn Ala Glu Ile Arg Arg Gly Ala Val Val Gly Asn Gly
    610                 615                 620

Asn Val Leu Ala Ala Tyr Asp Arg Arg Thr Arg Ser Glu Val Ala Arg
625                 630                 635                 640

Ala Asp Leu Leu Ala Val Leu Lys Gly Leu Ser Arg Leu Ala Met Ala
                645                 650                 655

Gly Ser Val Arg Val Tyr Ser Ala Thr Gln Ala Gly Asn Asp Gln Ala
            660                 665                 670

Asp Val Asn Val Leu Arg Ser Asp Gly Lys Ser Gly Pro Ser Ala Arg
        675                 680                 685
```

```
Ile Met Glu Ile Gly Thr Leu Val Glu Arg Arg Gly Ser Ala Ala Asp
    690             695                 700

Ala Gly Ala Asp Ala Ser Gly Ala Ala Val Ser Ser Gly Val Ala Ala
705             710                 715                 720

Asp Thr Gly Gln Pro Val Thr Leu Ala Gly Ala Asp Glu Leu Trp Ala
                725                 730                 735

Thr Leu Arg Arg Leu Val Arg
            740
```

The invention claimed is:

1. An isolated mycovirus exhibiting an action of suppressing rice blast fungus and comprising four double-stranded RNA sequences, each sequence having a length of from 2.8 to 3.6 kb.

2. The isolated mycovirus according to claim 1, suppressing conidia formation by the rice blast fungus.

3. The isolated mycovirus according to claim 1, having a double-stranded RNA homologous to a region encoding RdRp (RNA-dependent RNA polymerase) in a Chrysoviridae virus genome.

4. The isolated mycovirus according to claim 1, suppressing rice blast fungus of a plant of the family Poaceae.

5. The isolated mycovirus according to claim 1, wherein the first double-stranded RNA sequence comprises the base sequence depicted in SEQ ID NO: 1, the second double-stranded RNA sequence comprises the base sequence depicted in SEQ ID NO: 2, the third double-stranded RNA sequence comprises the base sequence depicted in SEQ ID NO: 3, the fourth double-stranded RNA sequence comprises the base sequence depicted in SEQ ID NO: 4, wherein in each of SEQ ID NO:s 1-4, thymine is replaced by uracil.

6. A plant disease control agent comprising at least one selected from the group consisting of an isolated mycovirus exhibiting an action of suppressing rice blast fungus and comprising four double-stranded RNA sequences each sequence having a length of from 2.8 to 3.6 kb and an attenuated strain of a phytopathogenic fungus comprising an isolated mycovirus exhibiting an action of suppressing rice blast fungus and comprising four double-stranded RNA sequences each sequence having a length of from 2.8 to 3.6 kb.

7. The isolated mycovirus according to claim 1, wherein the mycovirus is isolated from fungal host cells.

8. An isolated mycovirus exhibiting an action of suppressing rice blast fungus, comprising four double-stranded RNA sequences each sequence having a length of from 2.8 to 3.6 kb, wherein the isolated mycovirus is obtained from excretions of a host fungus and wherein the isolated mycovirus is infectious.

* * * * *